United States Patent [19]

Hashimoto et al.

[11] Patent Number: 4,883,800
[45] Date of Patent: Nov. 28, 1989

[54] QUINAZOLINE DERIVATIVES AND PROCESS FOR THEIR PRODUCTION

[75] Inventors: Masashi Hashimoto; Teruo Oku; Yoshikuni Ito; Takayuki Namiki; Kozo Sawada; Chiyoshi Kasahara; Yukihisa Baba, all of Ibaraki, Japan

[73] Assignee: Fujisawa Pharmaceutical Co., Ltd., Osaka, Japan

[21] Appl. No.: 130,297

[22] Filed: Dec. 8, 1987

Related U.S. Application Data

[62] Division of Ser. No. 908,005, Sep. 16, 1986, Pat. No. 4,734,419.

[30] Foreign Application Priority Data

Oct. 7, 1985 [GB] United Kingdom ............... 8524663

[51] Int. Cl.⁴ .................. A61K 31/505; C07D 239/80
[52] U.S. Cl. ................................. 514/259; 514/223.2; 544/12; 544/284; 544/285
[58] Field of Search .............. 544/284, 285, 12, 259; 514/222

[56] References Cited

U.S. PATENT DOCUMENTS 4,016,166  4/1977  Noda et al. ................... 544/284
4,405,623  9/1983  Ishikawa et al. .............. 544/284
4,490,374  12/1984  Bandurco et al. ............. 544/284

FOREIGN PATENT DOCUMENTS 0089065  9/1983  European Pat. Off. .
2652144  5/1978  Fed. Rep. of Germany .
232702   2/1986  Fed. Rep. of Germany .

OTHER PUBLICATIONS

A. Lespagnol et al.: (I) Annales pharmaceutiques francaises, 1974, 32, No. 2, pp. 125-132.
A. Lespagnol et al.: II Eur. J. Med. Chem.-Chimica Therapeutica, May-Jun. 1974-9, No. 3, pp. 263-268.

*Primary Examiner*—Glennon H. Hollrah
*Assistant Examiner*—James H. Turnipseed
*Attorney, Agent, or Firm*—Oblon, Spivak, McClelland, Maier & Neustadt

[57] ABSTRACT

The invention relates to compounds having aldose reductase-inhibitory activity of the formula:

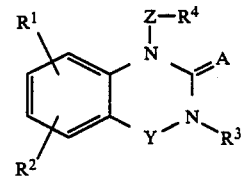

in which $R^1$ and $R^2$ are each hydrogen, halogen, lower alkoxy or halo(lower)alkyl,
 $R^3$ is phenyl(lower)alkyl which may have one or more substituent(s) selected from the group consisting of halogen, lower alkoxy, halo(lower)alkyl and lower alkyl,
 $R^4$ is carboxy or protected carboxy,
 A is sulfur atom,
 Y is carbonyl, thiocarbonyl or sulfonyl and
 Z is lower alkylene,
and pharmaceutically acceptable salts thereof, useful in treating diabetic complications.

7 Claims, No Drawings

QUINAZOLINE DERIVATIVES AND PROCESS FOR THEIR PRODUCTION

This is a division of application Ser. No. 06/908,005, filed Sept. 16, 1986, now U.S. Pat. No. 4,734,419.

This invention relates to new quinazoline derivatives. More particularly, this invention relates to new quinazoline derivatives and pharmaceutically acceptable salts thereof, which have an aldose reductase-inhibitory activity, to a process for their production, to a pharmaceutical composition containing the same and to a use thereof for manufacture of medicaments.

Accordingly, one object of this invention is to provide new and useful quinazoline derivatives and pharmaceutically acceptable salts thereof.

Another object of this invention is to provide a process for production of the quinazoline derivatives and salts thereof.

A further object of this invention is to provide a pharmaceutical composition containing, as an active ingredient, said quinazoline derivatives or pharmaceutically acceptable salts thereof.

Still further object of this invention is to provide a use of the quinazoline derivatives and pharmaceutically acceptable salts thereof for manufacture of medicaments for the therapeutic treatment of diabetic complications such as corneal wound healing defects, cataract, neuropathy, retinopathy, nephropathy.

The new quinazoline derivatives of this invention can be represented by the following general formula:

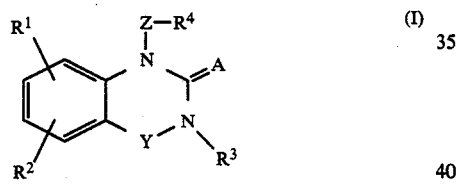

(I)

in which
$R^1$ and $R^2$ are each hydrogen, halogen, lower alkoxy or halo(lower)alkyl,
$R^3$ is aryl or ar(lower)alkyl, both of which may have one or more suitable substituent(s), or heterocyclic(lower)alkyl,
$R^4$ is carboxy or protected carboxy,
A is oxygen or sulfur atom,
Y is carbonyl, thiocarbonyl or sulfonyl and
Z is lower alkylene.

Suitable salts of the object compounds (I) are conventional pharmaceutically acceptable salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), a salt with a basic amino acid (e.g. arginine, etc.); and the like.

According to this invention, the object quinazoline derivatives (I) and salts thereof can be prepared by the processes as illustrated in the following.

Process 1:

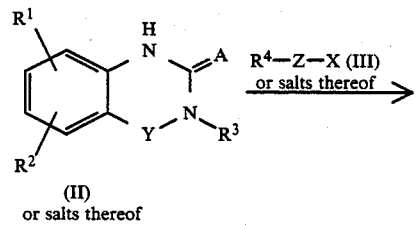

(II) or salts thereof $R^4-Z-X$ (III) or salts thereof →

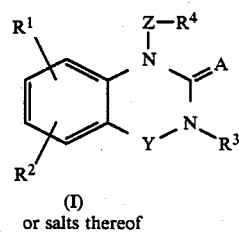

(I) or salts thereof

Process 2:

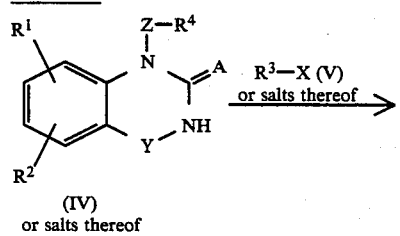

(IV) or salts thereof $R^3-X$ (V) or salts thereof →

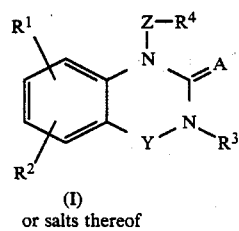

(I) or salts thereof

Process 3:

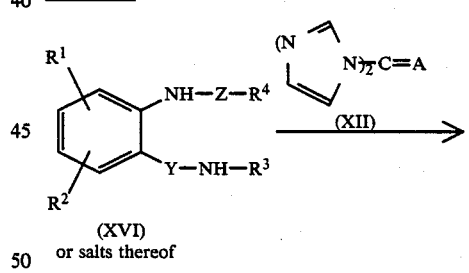

(XVI) or salts thereof (XII) →

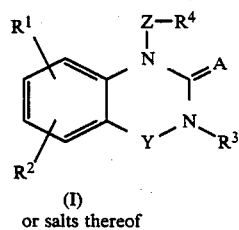

(I) or salts thereof

Process 4:

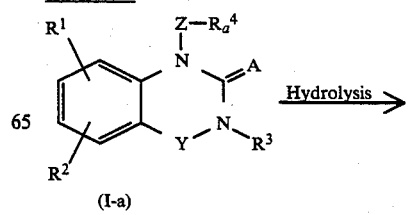

(I-a)

Hydrolysis →

-continued

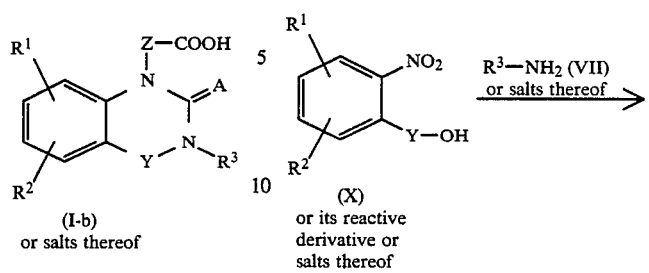

(I-b)
or salts thereof in which

R¹, R², R³, R⁴, A, Y and Z are as defined above, $R_a^4$ is protected carboxy and X is a leaving group.

The starting compounds (II), (IV) and (XVI) of the above processes contain new and known compounds, and the new compounds can be prepared, for example, by the following methods.

Method A-1:

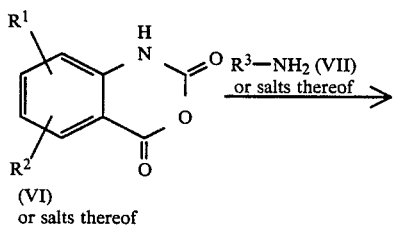

(VI)
or salts thereof

Method A-2:

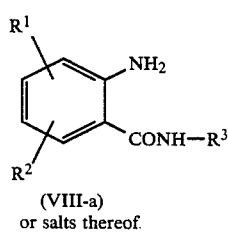

(VIII-a)
or salts thereof

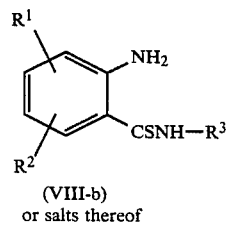

(VIII-b)
or salts thereof

Method A-3:

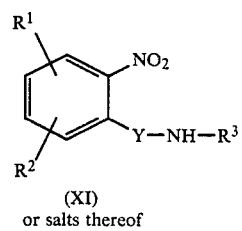

(X)
or its reactive derivative or salts thereof

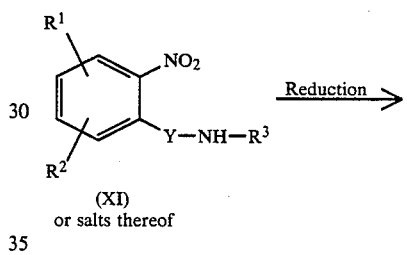

(XI)
or salts thereof

Method A-4:

(XI)
or salts thereof

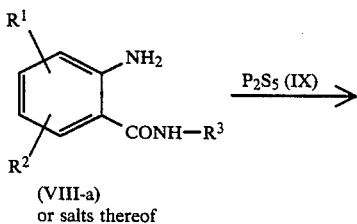

(VIII)
or salts thereof

Method A-5:

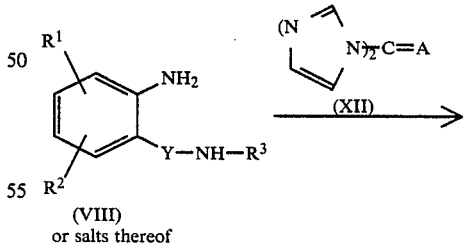

(VIII)
or salts thereof

(II)

Method B-1:

-continued

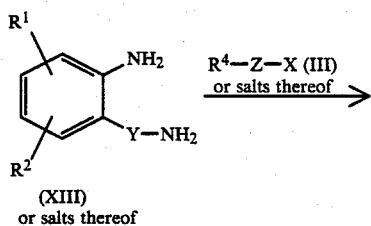
(XIII)
or salts thereof

→ R⁴—Z—X (III) or salts thereof →

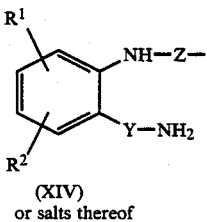
(XIV)
or salts thereof

Method B-2:

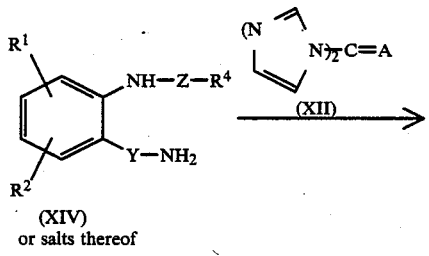
(XIV)
or salts thereof

→

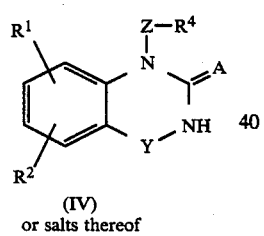
(IV)
or salts thereof

Method B-3:

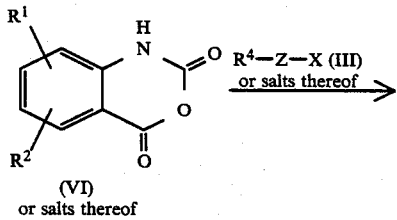
(VI)
or salts thereof

→ R⁴—Z—X (III) or salts thereof →

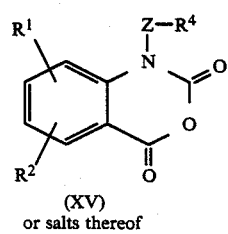
(XV)
or salts thereof

Method B-4:

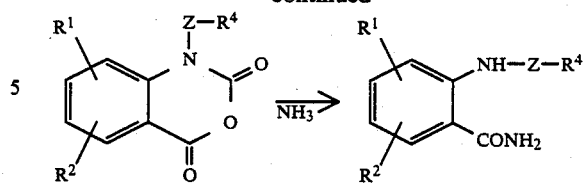
(XV)
or salts thereof

→ NH₃ →

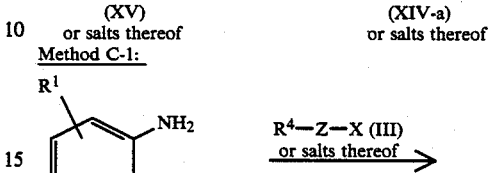
(XIV-a)
or salts thereof

Method C-1:

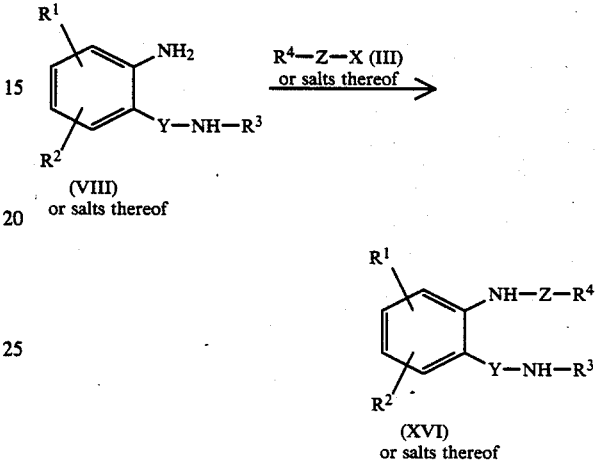

Method C-2:

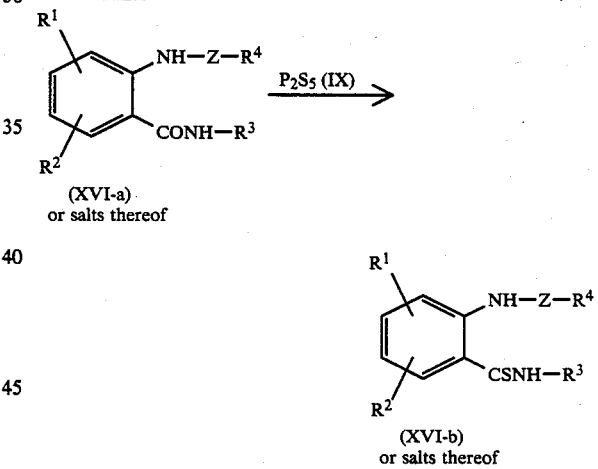

in which R¹, R², R³, R⁴, A, X, Y and Z are as defined above.

In the above and subsequent description of the present specification, suitable examples of the various definitions to be included within the scope thereof are explained in detail as follows.

The term "lower" used in the specification is intended to mean 1 to 6 carbon atoms, unless otherwise indicated.

Suitable "halogen" may include fluorine, chlorine, bromine, iodine, and the like.

Suitable "lower alkoxy" may include straight or branched one such as methoxy, ethoxy, propoxy, isopropoxy, butoxy, isobutoxy, pentyloxy, isopentyloxy, hexyloxy, and the like, in which more preferred example may be $C_1$–$C_4$ alkoxy and the most preferred one may be methoxy.

Suitable "halo(lower)alkyl" may include monohalo(lower)alkyl (e.g. chloromethyl, bromomethyl, chloropropyl, etc.), dihalo(lower)alkyl (e.g. 1,2-dichloroethyl, 1,2-dibromoethyl, 2,2-dichloroethyl, etc.), trihalo(lower)alkyl (e.g. trifluoromethyl, 1,2,2-trichloroethyl, etc.), in which more preferred one may be trihalo($C_1$-$C_4$)alkyl and the most preferred one may be trifluoromethyl.

Suitable "aryl" may include phenyl, tolyl, xylyl, cumenyl, mesityl, naphthyl, and the like, and these groups may have one or more suitable substituent(s) such as halogen as aforementioned. The preferred example of the aryl group thus defined may be dihalophenyl and the most preferred one may be dichlorophenyl.

Suitable "ar(lower)alkyl" may include benzyl, phenethyl, phenylpropyl, phenylbutyl, phenylpentyl, phenylhexyl, naphthylmethyl, naphthylpropyl, benzhydryl, trityl, and the like, and these groups may have one or more suitable substituent(s) such as halogen, lower alkoxy and halo(lower)alkyl as aforementioned, lower alkyl (e.g. methyl, ethyl, propyl, isopropyl, butyl, isobutyl, tert-butyl, pentyl, hexyl, etc.), and the like. The preferred example of the ar(lower)alkyl thus defined may be phenyl($C_1$-$C_4$)alkyl, naphthyl($C_1$-$C_4$)alkyl, and phenyl($C_1$-$C_4$)alkyl substituted by one or two substituent(s) selected from the groups consisting of halogen, $C_1$-$C_4$ alkoxy, $C_1$-$C_4$ alkyl and trihalo($C_1$-$C_4$)alkyl, and the most preferred one may be benzyl, naphthylmethyl, 4-chlorobenzyl, 2,3-(or 2,4- or 2,5- or 2,6- or 3,4- or 3,5-)dichlorobenzyl, 4-chloro-2-fluorobenzyl, 4-bromo-2-fluorobenzyl, 2-fluoro-3(or 4)-iodobenzyl, 4-bromo-3-chlorobenzyl, 4-methoxybenzyl, 4-methylbenzyl, 4-chloro-3-methoxy (or 3-trifluoromethyl)benzyl, 3-chloro-4-iodo(or 4-methoxy)benzyl and 3,5-bis(trifluoromethyl)benzyl.

Suitable "lower alkyl" moiety of the "heterocyclic(lower)alkyl" may include straight or branched one such as those aforementioned, and suitable "heterocyclic" moiety of the same may include saturated or unsaturated, monocyclic or polycyclic heterocyclic group containing at least one hetero atom such as an oxygen, sulfur nitrogen atom, and the like, and more preferable heterocyclic moiety may be heterocyclic group such as aromatic 5 or 6-membered heteromonocyclic group containing 1 to 4 nitrogen atom(s), preferably one nitrogen atom, or 1 to 2 sulfur atom(s), preferably one sulfur atom, for example, pyridyl, thienyl, and the like.

The preferred example of "heterocyclic(lower)alkyl" thus defined may be pyridylmethyl, pyridylethyl, pyridylpropyl, pyridylbutyl, pyridylpentyl, pyridylhexyl, thienylmethyl, thienylethyl, thienylpropyl, thienylbutyl, thienylpentyl, thienylhexyl, and the like, in which more preferred example may be pyridyl($C_1$-$C_4$)alkyl and thienyl($C_1$-$C_4$)alkyl, and the most preferred one may be pyridylmethyl and thienylmethyl.

Suitable "protected carboxy" may include esterified carboxy such as lower alkoxycarbonyl (e.g. methoxycarbonyl, ethoxycarbonyl, propoxycarbonyl, isopropoxycarbonyl, butoxycarbonyl, tert-butoxycarbonyl, etc.), mono(or di or tri)phenyl(lower)alkoxycarbonyl whcih may have a nitro group (e.g. benzyloxycarbonyl, 4-nitrobenzyloxycarbonyl, phenethyloxycarbonyl, benzhydryloxycarbonyl, trityloxycarbonyl, etc.), and the like, in which more preferred example may be $C_1$-$C_4$ alkoxycarbonyl and the most preferred one may be ethoxycarbonyl.

Suitable "lower alkylene" may include straight or branched one such as methylene, ethylene, trimethylene, tetramethylene, pentamethylene, hexamethylene, methylmethylene, ethylethylene, propylene, and the like, in which more preferred example may be $C_1$-$C_4$ alkylene and the most preferred one may be methylene and methylmethylene.

Suitable "leaving group" may include hydroxy and acid residue, and suitable example of "acid residue" may be halogen (e.g. chlorine, bromine, iodine, etc.), sulfonyloxy (e.g. methansulfonyloxy, benzenesulfonyloxy, toluenesulfonyloxy, etc.), and the like, in which the preferred example may be halogen.

The processes for production of the quinazoline derivatives (I) of this invention are explained in detail in the following.

(1) Process 1

The compounds (I) or salts thereof can be prepared by reacting the compound (II) or salts thereof with the compound (III) or salts thereof.

Suitable salts of the compounds (II) and (III) may be the same as those for the compounds (I).

Preferable examples of the compound (III) to be used in this process may be lower alkyl ester of halo(lower)alkanoic acid (e.g. methyl chloroacetate, methyl bromoacetate, ethyl chloroacetate, ethyl bromoacetate, propyl bromoacetate, t-butyl chloroacetate, ethyl 3-chloropropionate, ethyl 3-bromopropionate, ethyl 2-chloropropionate, ethyl 2-bromopropionate, etc.), lower alkoxycarbonyl(lower)alkyl ester of sulfonic acid (e.g. ethoxycarbonylmethyl methansulfonate, 1-ethoxycarbonylethyl methansulfonate, ethoxycarbonylmethyl benzenesulfonate, 1-ethoxycarbonylethyl benzenesulfonate, ethoxycarbonylmethyl toluenesulfonate, 1-ethoxycarbonylethyl toluenesulfonate, etc.), and the like.

This reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-dimethylaminopyridine, etc.), quinoline, and the like.

This reaction is usually carried out in a conventional solvent which does not adversely influence the reaction such as dichloromethane, methanol, ethanol, propanol, pyridine, N,N-dimethylformamide, etc., or a mixture thereof.

The reaction temperature is not critical and the reaction is usually carried out under from cooling to heating.

(2) Process 2

The compounds (I) or salts thereof can be prepared by reacting the compound (IV) or salts thereof with the compound (V) or salts thereof.

Suitable salts of the compounds (IV) and (V) may be the same as those for the compounds (I).

This reaction is preferably carried out in the presence of an organic or inorganic base such as those given in the explanation of the Process 1.

This reaction can be carried out in substantially the same manner as that of the Process 1, and therefore the reaction method and conditions (e.g. solvent, reaction temperature, etc.) are to be referred to the explanation of the Process 1.

(3) Process 3

The compounds (I) or salts thereof can be prepared by reacting the compounds (XVI) or salts thereof with the compound (XII).

Suitable salts of the compounds (XVI) may be the same as those for the compounds (I).

This reaction is usually carried out in the presence or absence of a conventional solvent which does not adversely influence the reaction such as acetone, benzene, tetrahydrofuran, pyridine, N,N-dimethylformamide, dioxane, etc., or a mixture thereof.

The reaction temperature is not critical and the reaction is usually carried out under from cooling to heating.

(4) Process 4

The compounds (I-b) or salts thereof can be prepared by hydrolyzing the compounds (I-a).

Suitable salts of the compounds (I-b) may be the same as those for the compounds (I).

The hydrolysis can be carried out in the presence of a base or an acid, and suitable base may be the inorganic base such as those given in the Process 1. Suitable acid may be an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.).

This reaction is usually carried out in a conventional solvent which does not adversely influence the reaction such as water, acetone, dichloromethane, methanol, ethanol, propanol, pyridine, N,N-dimethylformamide, etc., or a mixture thereof, and further in case that the base or acid to be used in this reaction is in liquid, it can also be used as a solvent.

The reaction temperature is not critical and the reaction is usually carried out under from cooling to heating.

Methods A, B and C for the production of new starting compounds (II), (IV), (XVI) and their intermediary compounds are explained in detail in the following.

(1) Method A-1

The compound (VIII-a) or salts thereof can be prepared by reacting the compound (VI) or salts thereof with the compound (VII) or salts thereof.

Suitable salts of the compound (VIII-a) may be salts formed with a base such as those for the compounds (I), salts formed with an acid such as an inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, toluenesulfonate, etc.).

Suitable salts of the compound (VI) may be the same as those for the compounds (I).

Suitable salts of the compound (VII) may be acid addition salts as exemplified for the compound (VIII-a).

This reaction is usually carried out in a conventional solvent which does not adversely influence the reaction such as acetone, benzene, tetrahydrofuran, pyridine, N,N-dimethylformamide, etc., or a mixture thereof.

The reaction temperature is not critical and the reaction is usually carried out under from cooling to heating.

(2) Method A-2

The compound (VIII-b) or salts thereof can be prepared by reacting the compound (VIII-a) or salts thereof with the compound (IX).

Suitable salts of the compound (VIII-b) may be the same as those for the compound (VIII-a).

This reaction is usually carried out in a conventional solvent which does not adversely influence the reaction such as dichloromethane, methanol, ethanol, propanol, pyridine, N,N-dimethylformamide, dioxane, etc., or a mixture thereof.

The reaction temperature is not critical and the reaction is usually carried out under from cooling to warming.

(3) Method A-3

The compound (XI) or salts thereof can be prepared by reacting the compound (X) or its reactive derivative or salts thereof with the compound (VII) or salts thereof.

Suitable reactive derivative of the compound (X) may include acid halide such as acid chloride, acid bromide, etc., acid anhydride such as a mixed acid anhydride with an acid (e.g. phosphoric acid, dialkylphosphorous acid, sulfurous acid, sulfuric acid, alkyl carbonate, aliphatic carboxylic acid, aromatic carboxylic acid, etc.), an activated acid amide with a heterocyclic compound (e.g. imidazole, triazole, etc.), an activated ester (e.g. cyanomethyl ester, 2,4-dinitrophenylester, etc.), and the like, in which more preferable example may be acid halide and an activated acid amide with an aforementioned heterocyclic compound, and the most preferable one may be acid chloride and an activated acid amide with imidazole.

Suitable salts of the compounds (XI) and (X) may be the same as those for the compounds (I).

The reaction may be preferably carried out in the presence of an inorganic or an organic base such as an alkali metal hydroxide (e.g. sodium hydroxide, potassium hydroxide, etc.), an alkali metal carbonate (e.g. sodium carbonate, potassium carbonate, etc.), an alkali metal bicarbonate (e.g. sodium bicarbonate, potassium bicarbonate, etc.), tri(lower)alkylamine (e.g. trimethylamine, triethylamine, etc.), pyridine or its derivative (e.g. picoline, lutidine, 4-dimethylaminopyridine, etc.), and the like.

In this reaction, when the compound (X) is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide (e.g. ethyl chloroformate, isobutyl chloroformate, etc.), 1-(p-chlorobenzenesulfonyloxy)-6-chloro-1H-benzotriazole, and the like.

Further, this reaction is usually carried out in a conventional solvent which does not adversely influence the reaction such as acetone, dichloromethane, chloroform, pyridine, N,N-dimethylformamide, etc., or a mixture thereof. In case that the base or the condensing agent to be used is liquid, it can also be used as a solvent.

The reaction temperature is not critical and the reaction is usually carried out under from cooling to heating.

(4) Method A-4

The compound (VIII) or salts thereof can be prepared by reducing the compound (XI) or salts thereof.

Suitable salts of the compound (VIII) may be the same as those for the compound (VIII-a).

The reduction of the compound (XI) can be carried out by a conventional method, for example, by using a reducing agent such as lithium aluminum hydride, stannous chloride, etc.; by chemical reduction using metal (e.g. zinc, iron, copper, etc.) and acid (e.g. hydrochloric acid, sulfuric acid, acetic acid, etc.), or by catalytic reduction. The catalytic reduction is usually carried out in the presence of a conventional catalyst, such as Raney nickel, palladium, platinum, rhodium, copper, and the like.

This reaction is usually carried out in a conventional solvent which does not adversely influence the reaction such as water, alcohol (e.g. methanol, ethanol, etc.), pyridine, N,N-dimethylformamide, etc., or a mixture thereof, and further in case that the acid to be used in the chemical reduction is in liquid, it can also be used as a solvent.

The reaction temperature is not critical and the reaction is usually carried out under from cooling to heating.

(5) Method A-5 and Method B-2

The compounds (II) and (IV) or salts thereof can be prepared by reacting the compounds (VIII) and (XIV) or salts thereof with the compound (XII), respectively.

Suitable salts of the compound (XIV) may be the same as those for the compound (VIII-a).

This reaction is usually carried out in the presence or absence of a conventional solvent which does not adversely influence the reaction such as acetone, benzene, tetrahydrofuran, pyridine, N,N-dimethylformamide, dioxane, etc., or a mixture thereof.

The reaction temperature is not critical and the reaction is usually carried out under from cooling to heating.

(6) Method B-1

The compound (XIV) or salts thereof can be prepared by reacting the compound (XIII) or salts thereof with the compound (III) or salts thereof.

Suitable salts of the compounds (XIII) may be the same as those for the compound (VIII-a).

This reaction is preferably carried out in the presence of an organic or inorganic base such as those given in the explanation of the Process 1.

This reaction can be carried out in substantially the same manner as that of the Process 1, and therefore the reaction method and conditions (e.g. solvent, reaction temperature, etc.) are to be referred to the explanation of the Process 1.

(7) Method B-3

The compound (XV) or salts thereof can be prepared by reacting the compound (VI) or salt thereof with the compound (III) or salts thereof.

Suitable salts of the compound (XV) may be the same as those for the compounds (I).

This reaction can be carried out in substantially the same manner as that of the Process 1, and therefore the reaction method and conditions (e.g. solvent, reaction temperature, etc.) are to be referred to the explanation of the Process 1.

The reaction product of this process can be used in the next process with or without isolation and/or purification.

(8) Method B-4

The compound (XIV-a) or salts thereof can be prepared by reacting the compound (XV) or salts thereof with $NH_3$.

Suitable salts of the compound (XIV-a) may be the same as those for the compound (XIV).

This reaction can be carried out in a conventional solvent which does not adversely influence the reaction such as water, methanol, ethanol, propanol, pyridine, N,N-dimethylformamide, toluene, dioxane, etc., or a mixture thereof.

The reaction temperature is not critical and the reaction is usually carried out under from cooling to warming.

(9) Method C-1

The compound (XVI) or salts thereof can be prepared by reacting the compound (VIII) or salts thereof with the compound (III) or salts thereof.

This reaction can be carried out in substantially the same manner as that of the Process 1, and therefore the reaction method and conditions (e.g. solvent, reaction temperature, etc.) are to be referred to the explanation of the Process 1.

(10) Method C-2

The compound (XVI-b) or salts thereof can be prepared by reacting the compound (XVI-a) or salts thereof with the compound (IX).

Suitable salts of the compounds (XVI-a) and (XVI-b) may be the same as those for the compound (XVI).

This reaction can be carried out in substantially the same manner as that of the Method A-2, and therefore the reaction method and conditions (e.g. solvent, reaction temperature, etc.) are to be referred to the explanation of the Method A-2.

The compounds obtained in the above Processes 1 to 4 and Methods A, B and C can be isolated and purified in a conventional manner, for example, extraction, precipitation, fractional chromatography, fractional crystallization, recrystallization, and the like.

The object compounds (I) thus prepared can be transformed into pharmaceutically acceptable salts by conventional methods, if desired.

The new quinazoline derivatives (I) and pharmaceutically acceptable salts thereof have been found to possess aldose reductase-inhibitory activity and are of value, for example, as medicaments for the therapeutic treatment of diabetic complications such as corneal wound healing defects, cataract, neuropathy, retinopathy, nephropathy, and especially cataract and neuropathy.

The aldose reductase-inhibitory activity values of some representative species of the quinazoline derivatives (I) are given below.

(A) in vitro test
(1) Enzymatic assay method:

| | |
|---|---|
| 0.5 M Phosphate buffer (pH 6.2) | 0.1 ml |
| 2.0 M Lithium sulfate | 0.2 ml |
| The compound of this invention mentioned below (3) (dissolved in physiological saline solution) | 0.1 ml |
| Enzyme solution [aldose reductase solution, | 0.5 ml |

-continued

| | |
|---|---|
| prepared as described below (2)] | |
| 60 mM D,L-glyceraldehyde | 0.05 ml |
| 2.5 mM Nicotinamide adenine dinucleotide phosphate (reduced form) (NADPH) | 0.05 ml |

The above reactants were mixed and reacted at 35° C. for 2 minutes and the decrease in amount of NADPH was measured with an Automatic Reaction Rate Analyzer Model LKB-8600 (Trademark, made by LKB Producter A.B.). The enzyme activity at a change in absorbance of 0.001 per minute was taken as unity.

(2) Method for preparing an enzyme solution

Rabbit eyes were enucleated and the lenses were collected. The lenses were homogenized with 3 volumes of distilled water at 4° C. (All the subsequent procedures were also performed at 4° C.) and centrifuged at 10,000 G for 60 minutes. The supernatant was dialyzed against 2 liters of 0.05M of saline solution and the dialyzed solution was used as the enzyme solution.

(3) Test compounds

① 2-[3-(3,4-Dichlorobenzyl)-1,2,3,4-tetrahydro-2,4-dioxoquinazolin-1-yl]acetic acid (hereinafter referred to as Compound A)

② 2-[3-(4-Bromo-2-fluorobenzyl)-1,2,3,4-tetrahydro-2,4-dioxoquinazolin-1-yl]acetic acid (hereinafter referred to as Compound B)

③ 2-[3-(4-Bromo-2-fluorobenzyl)-1,2,3,4-tetrahydro-7-methoxy-2,4-dioxoquinazolin-1-yl]acetic acid (hereinafter referred to as Compound C)

④ 2-[3-(2-Fluoro-4-iodobenzyl)-1,2,3,4-tetrahydro-2,4-dioxoquinazolin-1-yl]acetic acid (hereinafter referred to as Compound D)

⑤ 2-[7-Bromo-3-(4-bromo-2-fluorobenzyl)-1,2,3,4-tetrahydro-2,4-dioxoquinazolin-1-yl]acetic acid (hereinafter referred to as Compound E)

(4) Test results

The results are shown in the following table.

Each $IC_{50}$ value (M) represents the concentration of the compounds of this invention at which 50% of the aldose reductase activity is inhibited.

| Test compounds | $IC_{50}$ (M) |
|---|---|
| Compound A | $5.4 \times 10^{-9}$ |
| Compound B | $4.8 \times 10^{-9}$ |
| Compound C | $5.4 \times 10^{-9}$ |
| Compound D | $5.3 \times 10^{-9}$ |
| Compound E | $3.1 \times 10^{-9}$ |

(B) in vivo test

Inhibitory effect of drug on sorbitol accumulation in sciatic nerve:

(1) Test Method

Male Sprague-Dawley rats (6 weeks old) were fasted for 24 hours and then made diabetic by the intraperitoneal injection (2 ml/kg) of streptozotocin (75 mg/kg) dissolved in 2 mM citrate buffer (pH 4.5).

Seven days after streptozotocin injection, blood glucose value was measured by taking blood from tail vein. Rats with blood glucose value of >300 mg/dl were used as streptozotocin-induced diabetic animals.

Diabetic animals were divided at random into two groups (group (A) and group (B)).

Drug was suspended in 0.5% aqueous methylcellulose solution and orally administered to each rat in group (A) once a day for five days [hereinafter referred to as drug-treated diabetic rats].

Each of rats in group (B) and of normal rats was given the vehicle (0.5% aqueous methylcellulose solution) [hereinafter referred to as untreated diabetic rats and control rats, respectively].

Six hours after final administration of drug or vehicle, animals were killed and sorbitol content in sciatic nerve was assayed. Inhibitory percent of drug on sorbitol accumulation in sciatic nerve was calculated as follows.

$$I(\%) = \left(\frac{S - S_D}{S - N}\right) \times 100$$

I: Inhibitory percent
S: Sorbitol content in sciatic nerve of untreated diabetic rats.
$S_D$: Sorbitol content in sciatic nerve of drug-treated diabetic rats.
N: Sorbitol content in sciatic nerve of control rats.

(2) Test compounds

① Compound D
② Compound E
③ 2-[3-(4-Bromo-2-fluorobenzyl)-7-chloro-1,2,3,4-tetrahydro-2,4-dioxoquinazolin-1-yl]acetic acid (hereinafter referred to as Compound F)

(3) Test results

| Test compounds (drugs) | dosage (mg/kg) | I (%) |
|---|---|---|
| Compound D | 32 | 101 |
| Compound E | 32 | 103 |
| Compound F | 32 | 99 |

The pharmaceutical composition is provided in various forms such as solid preparations, semi-solid preparations and liquid preparations, which contain the active compounds of this invention, i.e., the compounds (I) or pharmaceutically acceptable salts thereof, together with an organic or inorganic carrier or/and excipient suitable for external, internal or local administration. This active compound is used in combination with harmless and pharmacologically acceptable auxiliary components to provide such suitable dosage form as tablets, pellets, capsules, suppositories, solutions, emulsions, suspensions, etc. Examples of such auxiliary components include those which can be effectively utilized in the production of solid, semi-solid or liquid preparations, for example, water, glucose, lactose, gelatin, mannitol, starch paste, magnesium trisilicate, corn starch, keratin, colloidal silica, potato starch, urea, etc. Furthermore, such auxiliaries as stabilizers, extenders, colorants and fragrances may also be incorporated. The pharmaceutical compositions according to this invention may also contain preservatives so that the activity of the active compound can be preserved. Said compositions should contain the active compound in an amount sufficient for the production of desirable therapeutic effects against the progress or actual condition of a disease concerned.

When the pharmaceutical compositions are applied to humans, they are desirably administered by the intravenous, intramuscular or oral route. The effective dose of each active compound depends on the age and/or symptom of the patient to be treated. Generally, however, the pharmaceutical preparations contain about 50 mg, 100 mg, 250 mg, 500 mg or 1000 mg of the active compound per unit dosage form and are administered to humans or animals at a daily dose of 0.1–100 mg per kilogram of body weight.

The following preparations and examples illustrate this invention in more detail.

PREPARATION 1

(1) A mixture of 2H-3,1-benzoxazine-2,4(1H)-dione (20 g) and 3,4-dichlorobenzylamine (16.4 ml) in benzene (200 ml) was refluxed for 3 hours. After cooling, the solvent was removed under reduced pressure to give a residue, which was recrystallized from n-hexane-ethyl acetate (1:2) to afford 2-amino-N-(3,4-dichlorobenzyl)-benzamide (30.5 g).

IR (Nujol): 3450, 3350, 3300, 1620 cm$^{-1}$;
NMR (DMSO-d$_6$, δ): 3.30 (2H, broad s), 4.30 (2H, d, J=7 Hz), 6.00–7.70 (7H, m), 8.70 (1H, t, J=7 Hz).

The following compound was obtained in substantially the same manner as that of Preparation 1-1).

(2) 2-Amino-N-(4-bromo-2-fluorobenzyl)benzamide
mp: 117°–117.5° C.;
IR (Nujol): 3470, 3350, 3270, 1765, 1730, 1610, 1585, 1540 cm$^{-1}$.
NMR (DMSO-d$_6$, δ): 4.40 (2H, d, J=6 Hz), 6.39 (2H, broad s), 6.4–6.8 (2H, m), 7.0–7.8 (5H, m), 8.70 (1H, t, J=6 Hz).

PREPARATION 2

A mixture of 2-amino-N-(3,4-dichlorobenzyl)benzamide (3.5 g) and phosphorus pentasulfide (4.74 g) in dioxane (56 ml) was stirred at room temperature for 5 hours. The reaction mixture was poured into an aqueous sodium bicarbonate and extracted with ethyl acetate. The extract was washed with water and dried. Evaporation of the solvent gave a residue, which was chromatographed on silica gel. Elution with chloroform followed by recrystallization from isopropyl ether gave 2-amino-N-(3,4-dichlorobenzyl)benzenecarbothioamide (1.56 g).
mp: 89°–91° C.
IR (Nujol): 3370, 1605 cm$^{-1}$.

PREPARATION 3

(1) To a solution of 3,4-dichlorobenzylamine (3.97 g) and triethylamine (3.5 ml) in chloroform (80 ml) was added a solution of 2-nitrobenzenesulfonyl chloride (5 g) in chloroform (20 ml) at 0° C. with stirring and the mixture was stirred for 30 minutes at the same temperature. The reaction mixture was washed successively with diluted hydrochloric acid and water, and then dried. Evaporation of the solvent gave N-(3,4-dichlorobenzyl)-2-nitrobenzenesulfonamide (6.87 g).

IR (Nujol): 3330, 1530, 1160 cm$^{-1}$.
NMR (DMSO-d$_6$, δ): 4.23 (2H, d, J=5 Hz), 7.15–8.03 (7H, m), 8.67 (1H, t, J=5 Hz).

The following compound was obtained in substantially the same manner as that of Preparation 3-1).

(2) N-(4-Bromo-2-fluorobenzyl)-3-methoxy-2-nitrobenzamide

IR (Nujol): 3300, 1640, 1610 cm$^{-1}$.
NMR (DMSO-d$_6$, δ): 3.95 (3H, s), 4.39 (2H, d, J=6 Hz), 7.13–7.63 (6H, m), 9.22 (1H, t, J=6 Hz).

PREPARATION 4

(1) A mixture of N-(3,4-dichlorobenzyl)-2-nitrobenzenesulfonamide (4 g) and iron (2 g) in acetic acid (30 ml) was stirred at 100° C. for 45 minutes. After cooling, the iron was filtered off. The filtrate was made alkaline with a diluted aqueous sodium hydroxide and extracted with ethyl acetate. The extract was washed with water, dried and evaporated. Recrystallization from ethyl ether gave 2-amino-N-(3,4-dichlorobenzyl)benzenesulfonamide (3.40 g).

IR (Nujol): 3500, 3380, 3290, 1615 cm$^{-1}$.
NMR (DMSO-d$_6$, δ): 3.99 (2H, s), 5.88 (2H, broad s), 6.44–7.54 (7H, m), 8.12 (1H, broad s).

The following compound was obtained in substantially the same manner as that of Preparation 4-1).

(2) 2-Amino-N-(4-bromo-2-fluorobenzyl)-3-methoxybenzamide.

IR (Nujol): 3500, 3380, 3300, 1630, 1600 cm$^{-1}$.
NMR (DMSO-d$_6$, δ): 3.82 (3H, s), 4.43 (2H, d, J=6 Hz), 6.12 (2H, broad s), 6.52–7.57 (6H, m), 8.72 (1H, t, J=6 Hz).

PREPARATION 5

(1) A mixture of 2-amino-N-(3,4-dichlorobenzyl)benzamide (0.295 g) and N,N'-carbonyldiimidazole (0.18 g) in benzene (3 ml) was refluxed for 15 minutes. After cooling, the resulting crystals were collected and washed with ethanol to give 3-(3,4-dichlorobenzyl)-1,2,3,4-tetrahydro-2,4-dioxoquinazoline (0.25 g).
mp: 274°–275° C.
IR (Nujol): 1710, 1660 cm$^{-1}$.
NMR (DMSO-d$_6$, δ): 5.07 (2H, s), 7.10–8.07 (7H, m), 11.50 (1H, broad s).

The following compounds were obtained in substantially the same manner as that of Preparation (5-1).

(2) 3-(4-Bromo-2-fluorobenzyl)-1,2,3,4-tetrahydro-2,4-dioxoquinazoline
mp: 251°–252° C.
IR (Nujol): 1720, 1660 cm$^{-1}$.
NMR (DMSO-d$_6$, δ): 5.15 (2H, s), 8.70–8.0 (7H, m), 11.50 (1H, broad s).

(3) 3-(3,4-Dichlorobenzyl)-1,2,3,4-tetrahydro-2-oxo-4-thioxoquinazoline.
mp: 287°–288° C.
IR (Nujol): 1690, 1590 cm$^{-1}$.
NMR (DMSO-d$_6$, δ): 5.73 (2H, s), 7.13–8.50 (7H, m), 12.03 (1H, broad s).

(4) 2-(3,4-Dichlorobenzyl)-3,4-dihydro-3-oxo-2H-1,2,4-benzothiadiazine 1,1-dioxide
IR (Nujol): 1695, 1600 cm$^{-1}$.
NMR (DMSO-d$_6$, δ): 5.00 (2H, s), 7.18–7.95 (7H, m), 11.53 (1H, broad s).

(5) 3-(4-Bromo-2-fluorobenzyl)-8-methoxy-1,2,3,4-tetrahydro-2,4-dioxoquinazoline.
IR (Nujol): 1720, 1660 cm$^{-1}$.

PREPARATION 6

(1) A mixture of 2-aminobenzamide (100 g), ethyl bromoacetate (97.74 ml) and potassium carbonate (253.78 g) in N,N-dimethylformamide (400 ml) was stirred at 60° C. for 4.5 hours. After cooling, the reaction mixture was poured into ice-water (2 l) and the resulting crystals were collected by filtration. Thus obtained product was purified by recrystallization from ethanol to give ethyl N-(2-carbamoylphenyl)aminoacetate (123.93 g).

mp: 147°–148° C.

IR (Nujol): 3380, 3180, 1740, 1635, 1615 cm$^{-1}$.

NMR (DMSO-d$_6$, δ): 1.22 (3H, t, J=7 Hz), 4.02 (2H, s), 4.14 (2H, q, J=7 Hz), 6.48–6.68 (2H, m), 7.11–7.68 (4H, m).

The following compounds were obtained in substantially the same manner as that of Preparation 6-1).

(2) Ethyl N-(2-carbamoyl-5-methoxyphenyl)aminoacetate.

IR (Nujol): 3420, 3390, 3320, 3240, 1725, 1655, 1625 cm$^{-1}$.

NMR (DMSO-d$_6$, δ): 1.20 (3H, t, J=7 Hz), 3.73 (3H, s), 4.00 (2H, d, J=5 Hz), 4.12 (2H, q, J=7 Hz), 6.00 (1H, dd, J=2, 8 Hz), 6.22 (1H, d, J=2 Hz), 7.23 (2H, broad s), 7.57 (1H, d, J=8 Hz), 8.73 (1H, t, J=5 Hz).

(3) Ethyl N-(2-carbamoyl-4-methoxyphenyl)aminoacetate.

mp: 108°–110° C.

IR (Nujol): 3375, 3200, 1720, 1645, 1600, 1510 cm$^{-1}$.

NMR (DMSO-d$_6$, δ): 1.20 (3H, t, J=7 Hz), 3.73 (3H, s), 3.92–4.28 (4H, m), 6.53 (1H, d, J=6 Hz), 6.97 (1H, dd, J=2, 6 Hz), 7.23 (1H, d, J=2 Hz), 7.98 (2H, m).

(4) Ethyl N-(2-carbamoyl-5-chlorophenyl)aminoacetate.

IR (Nujol): 3420, 1730, 1670, 1645, 1610 cm$^{-1}$.

NMR (DMSO-d$_6$, δ): 1.22 (3H, t, J=7 Hz), 4.14 (2H, q, J=7 Hz), 4.08 (1H, d, J=9 Hz), 4.82 (1H, d, J=9 Hz), 6.50–8.60 (6H, m).

(5) Ethyl N-(2-carbamoyl-4-chlorophenyl)aminoacetate.

mp: 139°–140° C.

IR (Nujol): 3400, 3225, 1720, 1650, 1615 cm$^{-1}$.

NMR (CDCl$_3$, δ): 1.28 (3H, t, J=7 Hz), 3.93 (2H, d, J=6 Hz), 4.23 (2H, q, J=7 Hz), 6.05 (2H, broad s), 6.47 (1H, d, J=9 Hz), 7.24 (1H, dd, J=2, 9 Hz), 7.40 (1H, d, J=2 Hz), 8.17 (1H, t, J=6 Hz).

(6) Ethyl N-(2-carbamoyl-3-chlorophenyl)aminoacetate.

mp: 151°–154° C.

IR (Nujol): 3370, 3180, 1750, 1645, 1615 cm$^{-1}$.

(7) Ethyl N-(2-carbamoyl-3-methoxyphenyl)aminoacetate mp: 138°–140° C.

IR (Nujol): 3425, 3310, 3180, 1735, 1630, 1605, 1590 cm$^{-1}$.

PREPARATION 7

(1) A mixture of ethyl N-(2-carbamoylphenyl)aminoacetate (54 g) and N,N'-carbonyldiimidazole (78.8 g) was stirred at 130° C. for 40 minutes. After cooling, the resulting crystals were collected by filtration and washed with ethanol to give ethyl 2-(1,2,3,4-tetrahydro-2,4-dioxoquinazolin-1-yl)acetate (54.96 g).

mp: 249°–250° C.

IR (Nujol): 3170, 3050, 1740, 1705, 1685, 1605 cm$^{-1}$.

NMR (DMSO-d$_6$, δ): 1.24 (3H, t, J=7 Hz), 4.16 (2H, q, J=7 Hz), 4.91 (2H, s), 7.13–8.10 (4H, m).

The following compounds were obtained in substantially the same manner as that of Preparation 7-1).

(2) Ethyl 2-(1,2,3,4-tetrahydro-7-methoxy-2,4-dioxoquinazolin-1-yl)acetate.

IR (Nujol): 3150, 1730, 1710, 1695, 1610 cm$^{-1}$.

NMR (DMSO-d$_6$, δ): 1.22 (3H, t, J=7 Hz), 3.87 (3H, s), 4.18 (2H, q, J=7 Hz), 4.92 (2H, s), 6.77 (1H, dd, J=2, 8 Hz), 6.93 (1H, d, J=2 Hz), 7.97 (1H, d, J=8 Hz).

(3) Ethyl 2-(1,2,3,4-tetrahydro-6-methoxy-2,4-dioxoquinazolin-1-yl)acetate.

mp: 260°–261° C.

IR (Nujol): 3175, 3050, 1740, 1705, 1670, 1480 cm$^{-1}$.

NMR (DMSO-d$_6$, δ): 1.22 (3H, t, J=7 Hz), 3.83 (3H, s), 4.20 (2H, q, J=7 Hz), 4.88 (2H, s), 7.32 (2H, m), 7.47 (1H, m), 11.73 (1H, broad s).

(4) Ethyl 2-(6-chloro-1,2,3,4-tetrahydro-2,4-dioxoquinazolin-1-yl)acetate.

mp: 251°–252° C.

IR (Nujol): 1735, 1700 (sh), 1690, 1610 cm$^{-1}$.

NMR (DMSO-d$_6$, δ): 1.60 (3H, t, J=7 Hz), 4.15 (2H, q, J=7 Hz), 4.90 (2H, s), 7.42 (1H, d, J=9 Hz), 7.78 (1H, dd, J=3, 9 Hz), 7.95 (1H, d, J=3 Hz), 11.90 (1H, broad s).

(5) Ethyl 2-(5-chloro-1,2,3,4-tetrahydro-2,4-dioxoquinazolin-1-yl)acetate.

mp: 233°–235° C.

IR (Nujol): 1735, 1720, 1690, 1590, 1580 cm$^{-1}$.

(6) Ethyl 2-(1,2,3,4-tetrahydro-5-methoxy-2,4-dioxoquinazolin-1-yl)acetate.

mp: 258°–260° C.

IR (Nujol): 3175, 1740, 1700, 1680, 1600, 1590 (sh) cm$^{-1}$.

PREPARATION 8

Ethyl N-(2-carbamoyl-5-chlorophenyl)aminoacetate (357 g) and N,N'-carbonyldiimidazole (451 g) were dissolved in 1,4-dioxane (1.5 l) and 1,4-dioxane was concentrated to about 0.5 l by distillation. The resulting mixture was stirred at 150° C. for 30 minutes. After cooling, the precipitated crystals were collected by filtration and washed with ethanol to give ethyl 2-(7-chloro-1,2,3,4-tetrahydro-2,4-dioxoquinazolin-1-yl)acetate (353 g).

IR (Nujol): 3200, 3070, 1740, 1710, 1690, 1605, 1580 cm$^{-1}$.

NMR (DMSO-d$_6$, δ): 1.23 (3H, t, J=7 Hz), 4.18 (2H, q, J=7 Hz), 4.92 (2H, s), 7.32 (1H, dd, J=2, 8 Hz), 7.55 (1H, d, J=2 Hz), 8.00 (1H, d, J=8 Hz).

PREPARATION 9

A mixture of 2-benzyloxycarbonylamino-4-chlorobenzoic acid (564 g) and phosphorus tribromide (1.5 kg) in diethyl ether (9 l) was refluxed for 40 hours and allowed to stand at room temperature for 5 days. The resulting precipitates were collected by filtration and washed in turn with diethyl ether (5 l) and ethanol (3 l) to give 7-chloro-2H-3,1-benzoxazine-2,4(1H)-dione (335 g).

mp: 282°–283° C. (dec.)

IR (Nujol): 3175, 1740 (broad), 1710, 1615 cm$^{-1}$.

NMR (DMSO-d$_6$, δ): 7.15 (1H, d, J=1.5 Hz), 7.30 (1H, dd, J=1.5, 5 Hz), 7.93 (1H, d, J=5 Hz), 11.83 (1H, s).

PREPARATION 10

To a suspension of 4,6-dichloroindolin-2,3-dione (5.95 g) in acetic acid (95 ml) was added chromium trioxide (16 g) over a period of 15 minutes at 60° C. with stirring and the mixture was stirred at 70°–75° C. for 1 hour. After cooling, the reaction mixture was poured into water (360 ml) and the resulting precipitates were collected by filtration. The filtrate was extracted with ethyl acetate. The extract was washed with water and dried. Removal of the solvent gave a residue, which was combined with the precipitates. Recrystallization from isopropyl ether gave 5,7-dichloro-2H-3,1-benzoxazine-2,4(1H)-dione (2.85 g).

mp: 267°–268° C.

IR (Nujol): 3225, 3200, 3100, 3075, 1790, 1775, 1705, 1610, 1585 cm$^{-1}$.

NMR (DMSO-d$_6$, δ): 7.09 (1H, d, J=1.2 Hz), 7.48 (1H, d, J=1.2 Hz).

PREPARATION 11

A mixture of 7-chloro-2H-3,1-benzoxazine-2,4(1H)-dione (18.4 g) and 4-bromo-2-fluorobenzylamine (26 g) in tetrahydrofuran (200 ml) was refluxed for 15 minutes. After cooling, tetrahydrofuran was evaporated to give a residue. Recrystallization from isopropyl ether gave 2-amino-N-(4-bromo-2-fluorobenzyl)-4-chlorobenzamide (26.6 g).

mp: 119.5° C.

IR (Nujol): 3460, 3350, 3260, 1625, 1605 cm$^{-1}$.

NMR (DMSO-d$_6$, δ): 4.4 (2H, d, J=5.6 Hz), 6.5–6.8 (4H, m), 7.3–7.6 (4H, m), 8.8 (1H, t, J=5.6 Hz).

PREPARATION 12

(1) To a solution of 4-bromo-2-fluorobenzylamine (2.3 g) and triethylamine (1.55 ml) in chloroform (40 ml) was added dropwise a solution of 4-bromo-2-nitrobenzoyl chloride (2.69 g) in chloroform (10 ml) at 0° C. with stirring and the mixture was stirred at the same temperature for 1 hour. The reaction mixture was washed in turn with diluted aqueous hydrochloric acid and water, and then dried. Evaporation of the solvent followed by recrystallization from diethyl ether gave 4-bromo-N-(4-bromo-2-fluorobenzyl)-2-nitrobenzamide (3.60 g).

mp: 192°–193° C.

IR (Nujol): 3275, 1650, 1605, 1555, 1535, 1485 cm$^{-1}$.

NMR (DMSO-d$_6$, δ): 4.42 (2H, d, J=5.7 Hz), 7.39–7.62 (4H, m), 8.02 (1H, dd, J=1.9, 8.2 Hz), 8.28 (1H, d, J=1.9 Hz), 9.29 (1H, t, J=5.7 Hz).

The following compounds were obtained in substantially the same manner as that of Preparation 12-1).

(2) N-(4-Bromo-2-fluorobenzyl)-4-iodo-2-nitrobenzamide.

mp: 204°–205° C.

IR (Nujol): 3270, 1645, 1580, 1570, 1535, 1485 cm$^{-1}$.

NMR (DMSO-d$_6$, δ): 4.42 (2H, d, J=6 Hz), 7.34–7.58 (4H, m), 8.17 (1H, d, J=1.3, 8 Hz), 8.36 (1H, d, J=1.3 Hz), 9.26 (1H, t, J=5.8 Hz).

(3) N-(4-Bromo-2-fluorobenzyl)-4-fluoro-2-nitrobenzamide.

mp: 157°–159° C.

IR (Nujol): 3250, 1620, 1540, 1360 cm$^{-1}$.

NMR (CDCl$_3$, δ): 4.62 (2H, d, J=5.9 Hz), 6.24 (1H, br s), 7.24–7.78 (6H, m).

(4) N-(4-Bromo-2-fluorobenzyl)-4-chloro-2-nitrobenzamide.

IR (Nujol): 3300, 1645, 1610, 1540, 1360 cm$^{-1}$.

(5) N-(4-Bromo-2-fluorobenzyl)-3-chloro-2-nitrobenzamide.

mp: 198°–200° C.

IR (Nujol): 3260, 1635 cm$^{-1}$.

NMR (DMSO-d$_6$, δ): 4.43 (2H, d, J=6 Hz), 7.23–8.07 (6H, m), 9.50 (1H, t, J=6 Hz).

(6) 4-Chloro-N-(4-chloro-3-(trifluoromethyl)benzyl]-2-nitrobenzamide.

mp: 151°–152° C.

IR (Nujol): 3260, 1640, 1600, 1550, 1530 cm$^{-1}$.

NMR (DMSO-d$_6$, δ): 4.55 (2H, d, J=6 Hz), 7.52–8.08 (5H, m), 8.17 (1H, d, J=2 Hz), 9.33 (1H, t, J=6 Hz).

(7) N-(4-Bromo-2-fluorobenzyl)-2-nitro-4-(trifluoromethyl)benzamide mp: 174°–175° C.

IR (Neat): 1640, 1530, 1400, 1360, 1320, 1120 cm$^{-1}$.

(8) 4-Fluoro-N-(2-fluoro-4-iodobenzyl)-2-nitrobenzamide

IR (Nujol): 3250, 3050, 1640, 1620, 1605, 1535, 1360 cm$^{-1}$.

NMR (DMSO-d$_6$, δ): 4.4 (2H, d, J=5.6 Hz), 7.2 (1H, dd, J=8, 8 Hz), 7.6–7.8 (5H, m), 8.0 (1H, dd, J=1.8, 8.6 Hz), 9.3 (1H, t, J=5.6 Hz).

(9) N-(2-Fluoro-4-iodobenzyl)-4-iodo-2-nitrobenzamide mp: 213°–214° C.

IR (Nujol): 3270, 3080, 1650, 1540, 1360, 860 cm$^{-1}$.

NMR (DMSO-d$_6$, δ): 9.29 (1H, t, J=5.8 Hz), 8.36–7.18 (6H, m), 4.41 (2H, d, J=5.8 Hz).

PREPARATION 13

A mixture of 4-bromo-2-nitrobenzoic acid (3.0 g) and N,N'-carbonyldiimidazole (2.37 g) in tetrahydrofuran (30 ml) was stirred at room temperature for 4 hours. To this mixture was added a solution of 2-fluoro-4-iodobenzylamine (3.37 g) in tetrahydrofuran (10 ml), and the resulting mixture was stirred at room temperature overnight. The reaction mixture was poured into a mixture of ethyl acetate and 0.5N hydrochloric acid. The organic layer was separated, washed successively with water, aqueous sodium bicarbonate, water and saturated aqueous sodium chloride, and dried over magnesium sulfate. The solvent was removed in vacuo and the crystalline residue was recrystallized from a mixture of ethyl acetate and hexane to give 4-bromo-N-(2-fluoro-4-iodobenzyl)-2-nitrobenzamide (4.88 g).

mp: 139°–140° C.

IR (Nujol): 3260, 1645 cm$^{-1}$.

NMR (DMSO-d$_6$, δ): 4.43 (2H, d, J=5.5 Hz), 7.23 (1H, t, J=8 Hz), 7.58–7.67 (3H, m), 8.03 (1H, dd, J=2,8 Hz), 8.28 (1H, d, J=2 Hz), 9.28 (1H, t, J=5.5 Hz).

PREPARATION 14

(1) A mixture of 4-bromo-N-(4-bromo-2-fluorobenzyl)-2-nitrobenzamide (3.4 g) and iron (1.45 g) in acetic acid (66 ml) was stirred at 100° C. for 30 minutes. After cooling, iron was filtered off. The filtrate was evaporated to give a residue, which was made alkaline with aqueous 1N sodium hydroxide and extracted with ethyl acetate. The extract was washed with water and dried. Removal of the solvent gave 2-amino-4-bromo-N-(4-bromo-2-fluorobenzyl)benzamide (3.10 g).

mp: 143°–144° C.

IR (Nujol): 3460, 3350, 3260, 1630, 1610, 1580, 1535, 1485 cm$^{-1}$.

NMR (DMSO-d$_6$, δ): 4.39 (2H, d, J=6 Hz), 6.64 (1H, d, J=1.5 Hz), 6.68 (2H, s), 6.92 (1H, d, J=1.5 Hz), 7.25–7.54 (4H, m), 8.85 (1H, t, J=5.8 Hz).

The following compounds were obtained in substantially the same manner as that of Preparation 14-1).

(2) 2-Amino-N-(4-bromo-2-fluorobenzyl)-4-iodobenzamide mp: 180° C.

IR (Nujol): 3450, 3350, 3275, 1635, 1605, 1570, 1535 cm$^{-1}$.

NMR (DMSO-d$_6$, δ): 4.39 (2H, d, J=6 Hz), 6.58 (2H, s), 6.84 (1H, d, J=8 Hz), 7.13 (1H, s), 7.25–7.54 (4H, m), 8.84 (1H, t, J=6 Hz).

(3) 2-Amino-N-(4-bromo-2-fluorobenzyl)-4-chlorobenzamide

IR (Nujol): 3460, 3350, 3260, 1625, 1605 cm $^{-1}$.

(4) 2-Amino-N-(4-bromo-2-fluorobenzyl)-3-chlorobenzamide mp: 170°–171° C.

IR (Nujol): 3480, 3375, 3290, 1625, 1605 cm$^{-1}$.

NMR (DMSO-d$_6$, δ): 4.43 (2H, d, J=6 Hz), 6.50 (2H, br. s), 6.57–7.70 (6H, m), 8.97 (1H, t, J=6 Hz).

(5) 2-Amino-4-chloro-N-[4-chloro-3-(trifluoromethyl)benzyl]benzamide mp: 122°–125° C.

IR (Nujol): 3450, 3300, 1630, 1580, 1525, 1480 cm$^{-1}$.

NMR (DMSO-d$_6$, δ): 4.48 (2H, d, J=6 Hz), 6.43–6.93 (4H, m), 7.47–7.90 (4H, m), 8.87 (1H, t, J=6 Hz).

(6) 2-Amino-4-bromo-N-(2-fluoro-4-iodobenzyl)benzamide mp: 111°–112° C.

IR (Nujol): 3400, 3300, 3270, 1630 cm$^{-1}$.

NMR (DMSO-d$_6$, δ): 4.43 (2H, d, J=5.5 Hz), 7.24 (1H, t, J=8 Hz), 7.57–7.67 (3H, m), 8.16 (1H, dd, J=2,8 Hz), 8.28 (1H, d, J=2 Hz), 9.28 (1H, t, J=5.5 Hz).

(7) 2-Amino-4-fluoro-N-(2-fluoro-4-iodobenzyl)benzamide

IR (Nujol): 3460, 3350, 3260, 1630, 1600 cm$^{-1}$.

NMR (DMSO-d$_6$, δ): 4.4 (2H, d, J=5.5 Hz), 6.3–6.5 (2H, m), 6.8 (2H, s), 7.1 (1H, dd, J=8, 8 Hz), 7.5–7.7 (3H, m), 8.8 (1H, t, J=5.5 Hz).

PREPARATION 15

(1) A solution of N-(4-bromo-2-fluorobenzyl)-4-fluoro-2-nitrobenzamide (4.79 g) and stannous chloride (12.24 g) in ethanol (26 ml) was stirred at 70°–80° C. for 30 minutes under an atmosphere of nitrogen. After cooling, the reaction mixture was poured into ice-cold water and neutralized with aqueous saturated sodium bicarbonate. The resulting precipitates were filtered off and washed with ethyl acetate. The filtrate was extracted with ethyl acetate and the extract was washed with water and dried. Removal of the solvent gave 2-amino-N-(4-bromo-2-fluorobenzyl)-4-fluorobenzamide (3.58 g).

mp: 120°–121° C.

IR (Nujol): 3250, 1610, 1520, 1360 cm$^{-1}$.

NMR (DMSO-d$_6$, δ): 4.41 (2H, d, J=5.6 Hz), 6.33 (1H, t, J=8.3 Hz), 6.47 (1H, d, J=8.3 Hz), 6.78 (2H, s), 7.67–7.27 (4H, m), 8.78 (1H, t, J=5.6 Hz).

The following compounds were obtained in substantially the same manner as that of Preparation 15-1).

(2) 2-Amino-N-(4-bromo-2-fluorobenzyl)-4-(trifluoromethyl)benzamide mp: 174°–175° C.

IR (Nujol): 1640, 1590, 1530, 1370 cm$^{-1}$.

(3) 2-Amino-N-(2-fluoro-4-iodobenzyl)-4-iodobenzamide mp: 178°–179° C.

IR (Nujol): 3470, 3150, 3260, 1630, 1600, 1570, 1530, 1300, 860, 720 cm$^{-1}$.

NMR (DMSO-d$_6$, δ): 4.44 (2H, d, J=5.5 Hz), 6.65–7.70 (6H, m), 8.89 (1H, t, J=5.5 Hz).

PREPARATION 16

(1) 2-Amino-4-bromo-N-(4-bromo-2-fluorobenzyl)benzamide (2.90 g) and N,N'-carbonyldiimidazole (4.68 g) were dissolved in dioxane (50 ml). The solution was evaporated to give a residue, which was stirred at 150° C. for 30 minutes. After cooling, the precipitates were collected by filtration and washed with ethanol to give 7-bromo-3-(4-bromo-2-fluorobenzyl)-1,2,3,4-tetrahydro-2,4-dioxoquinazoline (2.92 g).

mp: >280° C.

IR (Nujol): 1720, 1660, 1610, 1595, 1580, 1485 cm$^{-1}$.

NMR (DMSO-d$_6$, δ): 5.07 (2H, s), 7.19–7.86 (6H, m).

The following compounds were obtained in substantially the same manner as that of Preparation 16-1).

(2) 3-(4-Bromo-2-fluorobenzyl)-7-iodo-1,2,3,4-tetrahydro-2,4-dioxoquinazoline mp: >280° C.

IR (Nujol): 1715, 1660, 1605, 1590, 1580, 1485 cm$^{-1}$.

NMR (DMSO-d$_6$, δ): 5.06 (2H, s), 7.16 (1H, dd, J=8, 8 Hz), 7.32 (1H, d, J=8 Hz), 7.51–7.59 (3H, m), 7.66 (1H, d, J=8 Hz).

(3) 3-(4-Bromo-2-fluorobenzyl)-7-fluoro-1,2,3,4-tetrahydro-2,4-dioxoquinazoline mp: 250°–251° C.

IR (Nujol): 1720, 1660, 1600, 1360 cm$^{-1}$.

NMR (DMSO-d$_6$, δ): 5.08 (2H, s), 7.57–6.93 (5H, m), 8.01 (1H, dd, J=6, 7 Hz).

(4) 3-(4-Bromo-2-fluorobenzyl)-7-chloro-1,2,3,4-tetrahydro-2,4-dioxoquinazoline mp: >280° C.

IR (Nujol): 3200, 3060, 1720, 1660, 1615, 1600, 1580 cm$^{-1}$.

NMR (DMSO-d$_6$, δ): 5.1 (2H, s), 7.2–7.3 (4H, m), 7.5 (1H, d, J=8 Hz), 7.9 (1H, d, J=8 Hz).

(5) 3-(4-Bromo-2-fluorobenzyl)-8-chloro-1,2,3,4-tetrahydro-2,4-dioxoquinazoline mp: 288°–290° C.

IR (Nujol): 1715, 1660, 1610 cm$^{-1}$.

NMR (DMSO-d$_6$, δ): 5.10 (2H, s), 7.10–8.00 (6H, m).

(6) 7-Chloro-3-[4-chloro-3-(trifluoromethyl)benzyl]-1,2,3,4-tetrahydro-2,4-dioxoquinazoline mp: 239° C.

IR (Nujol): 1720, 1700, 1630 cm$^{-1}$.

NMR (DMSO-d$_6$, δ): 5.15 (2H, s), 7.07–7.40 (2H, m), 7.53–8.13 (4H, m).

(7) 3-(4-Bromo-2-fluorobenzyl)-7-trifluoromethyl-1,2,3,4-tetrahydro-2,4-dioxoquinazoline mp: 260°–261° C.

IR (Nujol): 1720, 1660, 1600, 1380, 1360, 1170, 1130 cm$^{-1}$.

PREPARATION 17

(1) A mixture of 2-amino-4-bromo-N-(2-fluoro-4-iodobenzyl)benzamide (3.80 g), N,N'-carbonyldiimidazole (5.5 g) and 1,4-dioxane (30 ml) was refluxed for 2 hours. The resulting crystals were collected by filtration, washed with 1,4-dioxane and dried over phosphorus pentoxide to give 7-bromo-3-(2-fluoro-4-iodobenzyl)-1,2,3,4-tetrahydro-2,4-dioxoquinazoline (2.85 g).

mp: 303°–304° C.

IR (Nujol): 1715, 1655 cm$^{-1}$.

NMR (DMSO-d$_6$, δ): 5.05 (2H, s), 7.00 (1H, t, J=8 Hz), 7.37 (2H, s), 7.46 (1H, t, J=8 Hz), 7.63 (1H, d, J=9 Hz), 7.85 (1H, d, J=9 Hz).

The following compounds were obtained in substantially the same manner as that of Preparation 17-1).

(2) 7-Fluoro-3-(2-fluoro-4-iodobenzyl)-1,2,3,4-tetrahydro-2,4-dioxoquinazoline

IR (Nujol): 1720, 1660, 1620, 1610, 1600 cm$^{-1}$.

NMR (DMSO-d$_6$, δ): 5.1 (2H, s), 6.9–7.1 (3H, m), 7.5 (1H, dd, J=1.4, 8.1 Hz), 7.6 (1H, dd, J=1.6, 9.7 Hz), 8.0 (1H, dd, J=6.2, 8.8 Hz).

(3) 3-(2-Fluoro-4-iodobenzyl)-7-iodo-1,2,3,4-tetrahydro-2,4-dioxoquinazoline mp: 320°–322° C.

IR (Nujol): 3470, 3360, 3270, 1720, 1660, 1600, 1480, 960, 860, 760 cm$^{-1}$.

NMR (DMSO-d$_6$, δ): 5.0 (2H, s), 7.0 (1H, t, J=8 Hz), 7.45–7.68 (5H, m).

PREPARATION 18

(1) Ethyl N-(2-carbamoyl-4,5-dichlorophenyl)aminoacetate (4.6 g) and N,N'-carbonyldiimidazole (5.12 g) were dissolved in dioxane (50 ml). The solution was evaporated to give a residue, which was stirred at 140° C. for 30 minutes. After cooling, the precipitates were collected by filtration and washed with ethanol to give ethyl 2-(6,7-dichloro-1,2,3,4-tetrahydro-2,4-dioxoquinazolin-1-yl)acetate (4.40 g).

mp: >280° C.

IR (Nujol): 1735, 1720, 1690, 1605, 1570 cm$^{-1}$.

NMR (DMSO-d$_6$, δ): 1.22 (3H, t, J=7 Hz), 4.17 (2H, q, J=7 Hz), 4.90 (2H, s), 7.86 (1H, s), 8.11 (1H, s).

The following compound was obtained in substantially the same manner as that of Preparation 18-1).

(2) Ethyl 2-(5,7-dichloro-1,2,3,4-tetrahydro-2,4-dioxoquinazolin-1-yl)acetate mp: 244°–247° C.

IR (Nujol): 1750, 1740 (sh), 1710, 1690, 1590, 1565 cm$^{-1}$.

NMR (DMSO-d$_6$, δ): 1.22 (3H, t, J=7 Hz), 4.18 (2H, q, J=7 Hz), 4.92 (2H, s), 7.49 (1H, s), 7.57 (1H, s), 11.89 (1H, s).

PREPARATION 19

(1) To a solution of 7-chloro-2H-3,1-benzoxazine-2,4(1H)-dione (330 g) in N,N-dimethylformamide (3.3 l) was added sodium hydride (60% in mineral oil, 86.8 g) below 20° C. and the mixture was stirred at 5° C. for 30 minutes. To this solution was added ethyl bromoacetate (222 ml) at 10° C. over a 30-minute period and the resulting mixture was stirred at room temperature for 1.5 hours. To this reaction mixture was added 28% aqueous ammonia (696 ml) below 10° C. and the resulting mixture was stirred at 5° C. for 20 minutes. The mixture was poured into 1N hydrochloric acid (16.5 l). The precipitates were collected by filtration, and washed in turn with water (3 times) and diethyl ether to give ethyl N-(2-carbamoyl-5-chlorophenyl)aminoacetate (360 g).

mp: 157°–155° C.

IR (Nujol): 3400, 1725, 1650, 1610 cm$^{-1}$.

NMR (DMSO-d$_6$, δ): 1.20 (3H, t, J=4.5 Hz), 4.05 (2H, d, J=4 Hz), 4.15 (2H, q, J=4.5 Hz), 6.58 (1H, d, J=1.5 Hz), 6.62 (1H, dd, J=1.5, 6 Hz), 7.63 (1H, d, J=6 Hz), 7.7 (2H, broad), 8.67 (1H, t, J=4 Hz).

The following compounds were obtained in substantially the same manner as that of Preparation 19-1).

(2) Ethyl N-(2-carbamoyl-4,5-dichlorophenyl)aminoacetate mp: 181° C.

IR (Nujol): 3400, 3360, 3225, 1720, 1655, 1620, 1570, 1505 cm$^{-1}$.

NMR (DMSO-d$_6$, δ): 1.21 (3H, t, J=7 Hz), 4.09 (2H, d, J=5.5 Hz), 4.15 (2H, q, J=7 Hz), 6.80 (1H, s), 7.86 (1H, s), 8.58 (1H, t, J=5.5 Hz).

(3) Ethyl N-(2-carbamoyl-3,5-dichlorophenyl)aminoacetate mp: 171°–173° C.

IR (Nujol): 3400 (sh), 3375, 3200, 1750, 1645, 1615, 1585, 1565 cm$^{-1}$.

NMR (DMSO-d$_6$, δ): 1.21 (3H, t, J=7 Hz), 3.99 (2H, d, J=5.5 Hz), 4.14 (2H, q, J=7 Hz), 5.87 (1H, t, J=5.5 Hz), 6.53 (1H, s), 6.78 (1H, s), 7.80 (1H, s), 7.98 (1H, s).

PREPARATION 20

(1) A mixture of 2-amino-N-benzylbenzamide (400 mg), ethyl bromoacetate (295 mg) and potassium carbonate (244 mg) in N,N-dimethylformamide (10 ml) was stirred at 100° C. for 17 hours. After cooling, the reaction mixture was poured into ice-cold water and extracted with diethyl ether. The extract was washed with water and dried. Removal of the solvent gave a residue, which was chromatographed on silica gel. Elution with chloroform gave ethyl 2-[2-(N-benzylcarbamoyl)anilino]acetate (137 mg).

IR (Nujol): 1735, 1630 cm$^{-1}$.

NMR (CDCl$_3$, δ): 3.25 (3H, t, J=7 Hz), 3.95 (2H, d, J=5 Hz), 4.20 (2H, q, J=7 Hz), 4.60 (2H, d, J=5 Hz), 6.60 (2H, d, J=8 Hz), 7.10–7.50 (9H, m), 8.00 (1H, br. s).

The following compound was obtained in substantially the same manner as that of Preparation 20-1).

(2) Ethyl 2-[2-{N-(3,4-dichlorobenzyl)carbamoyl}anilino]acetate

PREPARATION 21

A mixture of ethyl 2-[2-{N-(3,4-dichlorobenzyl)-carbamoyl}anilino]acetate (16.3 g), phosphorus pentasulfide (19.0 g) and 1,4-dioxane (320 ml) was refluxed for 1 hour. The reaction mixture was filtered and the filtrate was concentrated in vacuo. The residue was chromatographed on silica gel (300 g) eluting with chloroform to give ethyl 2-[2-{N-(3,4-dichlorobenzyl)thiocarbamoyl}anilino]acetate (13.72 g).

IR (CHCl$_3$): 3400, 1740 cm$^{-1}$.

NMR (CDCl$_3$, δ): 1.29 (3H, t, J=7 Hz), 3.83 (2H, s), 4.22 (2H, q, J=7 Hz), 4.96 (2H, d, J=5.5 Hz), 6.47 (1H, d, J=8 Hz), 6.67 (1H, dt, J=1,8 Hz), 7.12–7.29 (3H, m), 7.42–7.51 (2H, m), 8.23 (1H, t, J=5.5 Hz).

EXAMPLE 1

(1) To a suspension of 3-(3,4-dichlorobenzyl)-1,2,3,4-tetrahydro-2,4-dioxoquinazoline (1 g) in N,N-dimethylformamide (15 ml) was added sodium hydride (60% in mineral oil, 0.17 g) with stirring at 0° C. and the mixture was stirred for 15 minutes at the same temperature. To this mixture was added ethyl bromoacetate (0.45 ml) and the mixture was stirred for 1 hour at room temperature. The reaction mixture was poured into diluted hydrochloric acid and extracted with ethyl acetate. The extract was washed with brine, dried and evaporated to give a residue. Thus obtained product was purified by recrystallization from isopropyl ether to give ethyl 2-[3-(3,4-dichlorobenzyl)-1,2,3,4-tetrahydro-2,4-dioxoquinazolin-1-yl]acetate (1.21 g).

mp: 121°–122° C.

IR (Nujol): 1725, 1700, 1665, 1605 cm$^{-1}$.

The following compounds were obtained in substantially the same manner as that of Example 1-1).

(2) Ethyl 2-[3-(4-bromo-2-fluorobenzyl)-1,2,3,4-tetrahydro-2,4-dioxoquinazolin-1-yl)acetate mp: 153°–154° C.

IR (Nujol): 1735, 1715, 1665, 1605 cm$^{-1}$.

NMR (DMSO-d$_6$, δ): 1.15 (3H, t, J=7 Hz), 4.15 (2H, q, J=7 Hz), 4.97 (2H, s), 5.15 (2H, s), 7.0–8.2 (7H, m).

(3) Ethyl 2-[3-benzyl-1,2,3,4-tetrahydro-2,4-dioxoquinazolin-1-yl]acetate

IR (Nujol): 1740, 1700, 1660, 1650 cm$^{-1}$.

NMR (DMSO-d$_6$, δ): 1.30 (3H, t, J=7 Hz), 3.32 (2H, s), 4.25 (2H, q, J=7 Hz), 5.10 (2H, d, J=10 Hz), 7.30–8.30 (9H, m).

(4) Ethyl 2-[3-(3,4-dichlorophenyl)-1,2,3,4-tetrahydro-2,4-dioxoquinazolin-1-yl]acetate
IR (Nujol): 1740, 1710, 1665, 1605 cm$^{-1}$.
NMR (DMSO-d$_6$, δ): 1.23 (3H, t, J=7 Hz), 4.18 (2H, q, J=7 Hz), 4.97 (2H, s), 7.18-8.15 (7H, m).

(5) Ethyl 2-[3-(3,4-dichlorobenzyl)-1,2,3,4-tetrahydro-2,4-dioxoquinazolin-1-yl]propionate
mp: 130°-131° C.
IR (Nujol): 1735, 1700, 1655, 1605 cm$^{-1}$.

(6) Ethyl 2-[3-(3,4-dichlorobenzyl)-1,2,3,4-tetrahydro-2-oxo-4-thioxoquinazolin-1-yl]acetate
mp: 157°-158° C.
IR (Nujol): 1740, 1690, 1605, 1590 cm$^{-1}$.
NMR (CDCl$_3$, δ): 1.27 (3H, t, J=7 Hz), 4.25 (2H, q, J=7 Hz), 4.90 (2H, s), 5.85 (2H, s), 6.87-8.85 (7H, m).

(7) Ethyl 2-[2-(3,4-dichlorobenzyl)-3,4-dihydro-3-oxo-2H-1,2,4-benzothiadiazin-4-yl]acetate 1,1-dioxide
IR (CHCl$_3$): 1740, 1690, 1600 cm$^{-1}$.

(8) Ethyl 2-[3-(4-bromo-2-fluorobenzyl)-1,2,3,4-tetrahydro-8-methoxy-2,4-dioxoquinazolin-1-yl]acetate
IR (Nujol): 1755, 1745, 1700, 1660, 1600 cm$^{-1}$.
NMR (DMSO-d$_6$, δ): 1.22 (3H, t, J=7 Hz), 3.83 (3H, s), 4.18 (2H, q, J=7 Hz), 5.03 (2H, s), 5.17 (2H, s), 7.00-7.80 (6H, m).

(9) Ethyl 2-[3-(4-chlorobenzyl)-1,2,3,4-tetrahydro-2,4-dioxoquinazolin-1-yl]acetate
mp: 137° C.
IR (Nujol): 1730, 1700, 1670, 1605, 1480 cm$^{-1}$.

(10) Ethyl 2-[3-(2,6-dichlorobenzyl)-1,2,3,4-tetrahydro-2,4-dioxoquinazolin-1-yl]acetate
mp: 182°-183° C.
IR (Nujol): 1745, 1720, 1680, 1610, 1480 cm$^{-1}$.

(11) Ethyl 2-[3-(3,5-dichlorobenzyl)-1,2,3,4-tetrahydro-2,4-dioxoquinazolin-1-yl]acetate
mp: 122°-123° C.
IR (Nujol): 1730, 1700, 1660, 1600, 1570, 1480 cm$^{-1}$.

(12) Ethyl 2-[3-(2,4-dichlorobenzyl)-1,2,3,4-tetrahydro-2,4-dioxoquinazolin-1-yl]acetate
IR (Nujol): 1730, 1710, 1660, 1610 cm$^{-1}$.

(13) Ethyl 2-[3-(2,5-dichlorobenzyl)-1,2,3,4-tetrahydro-2,4-dioxoquinazolin-1-yl]acetate
IR (Nujol): 1740, 1705, 1660, 1605 cm$^{-1}$.

(14) Ethyl 2-[1,2,3,4-tetrahydro-3-(4-methoxybenzyl)-2,4-dioxoquinazolin-1-yl]acetate
mp: 135° C.
IR (Nujol): 1730, 1700, 1660, 1600, 1480 cm$^{-1}$.

(15) Ethyl 2-[1,2,3,4-tetrahydro-3-(1-naphthylmethyl)-2,4-dioxoquinazolin-1-yl]acetate
mp: 164°-167° C.
IR (Nujol): 1745, 1700, 1660, 1605 cm$^{-1}$.

(16) Ethyl 2-[1,2,3,4-tetrahydro-2,4-dioxo-3-(2-pyridylmethyl)quinazolin-1-yl]acetate
mp: 141°-143° C.
IR (Nujol): 1740, 1700, 1650, 1610 cm$^{-1}$.

(17) Ethyl 2-[3-(4-bromo-2-fluorobenzyl)-1,2,3,4-tetrahydro-7-methoxy-2,4-dioxoquinazolin-1-yl]acetate
IR (Nujol): 1740, 1690, 1650, 1610 cm$^{-1}$.

(18) Ethyl 2-[3-(4-bromo-2-fluorobenzyl)-1,2,3,4-tetrahydro-6-methoxy-2,4-dioxoquinazolin-1-yl]acetate
mp: 160°-160.5° C.
IR (Nujol): 1725, 1700, 1655, 1500, 1480 cm$^{-1}$.

(19) Ethyl 2-[3-(4-bromo-2-fluorobenzyl)-6-chloro-1,2,3,4-tetrahydro-2,4-dioxoquinazolin-1-yl]acetate
mp: 146°-147° C.
IR (Nujol): 1730, 1710, 1675, 1610 cm$^{-1}$.

(20) Ethyl 2-[3-(2-fluoro-4-iodobenzyl)-1,2,3,4-tetrahydro-2,4-dioxoquinazolin-1-yl]acetate
mp: 157° C.
IR (Nujol): 1750, 1705, 1670, 1610, 1480 cm$^{-1}$.

(21) Ethyl 2-[3-(4-chloro-2-fluorobenzyl)-1,2,3,4-tetrahydro-2,4-dioxoquinazolin-1-yl]acetate
mp: 144°-145° C.
IR (Nujol): 1730, 1705, 1660, 1610, 1480 cm$^{-1}$.

(22) Ethyl 2-[3-(4-bromo-3-chlorobenzyl)-1,2,3,4-tetrahydro-2,4-dioxoquinazolin-1-yl]acetate
mp: 128°-129° C.
IR (Nujol): 1735, 1700, 1660, 1600, 1480 cm$^{-1}$.

(23) Ethyl 2-[3-(2,3-dichlorobenzyl)-1,2,3,4-tetrahydro-2,4-dioxoquinazolin-1-yl]acetate
mp: 158°-160° C.
IR (Nujol): 1740, 1705, 1660, 1605, 1480 cm$^{-1}$.

(24) Ethyl 2-[1,2,3,4-tetrahydro-3-(4-methylbenzyl)-2,4-dioxoquinazolin-1-yl]acetate
mp: 140°-141° C.
IR (Nujol): 1735, 1700, 1660, 1605, 1480 cm$^{-1}$.

(25) Ethyl 2-[3-(4-chloro-3-methoxybenzyl)-1,2,3,4-tetrahydro-2,4-dioxoquinazolin-1-yl]acetate
IR (Nujol): 1740, 1705, 1660, 1610 cm$^{-1}$.

(26) Ethyl 2-[3-(3-chloro-4-methoxybenzyl)-1,2,3,4-tetrahydro-2,4-dioxoquinazolin-1-yl]acetate
IR (Nujol): 1730, 1700, 1660, 1605 cm$^{-1}$.

(27) Ethyl 2-[1,2,3,4-tetrahydro-2,4-dioxo-3-(2-thienylmethyl)quinazolin-1-yl]acetate
mp: 115°-120° C.
IR (Nujol): 1730, 1700, 1660, 1605 cm$^{-1}$.

(28) Ethyl 2-[1,2,3,4-tetrahydro-2,4-dioxo-3-(2-naphthylmethyl)quinazolin-1-yl]acetate
mp: 149°-150° C.

(29) Ethyl 2-[3-(4-bromo-2-fluorobenzyl)-5-chloro-1,2,3,4-tetrahydro-2,4-dioxoquinazolin-1-yl]acetate
mp: 186°-187° C.
IR (Nujol): 1740, 1710, 1670, 1590 cm$-1$.

(30) Ethyl 2-[3-(4-bromo-2-fluorobenzyl)-1,2,3,4-tetrahydro-5-methoxy-2,4-dioxoquinazolin-1-yl]acetate
mp: 166°-168° C.
IR (Nujol): 1735, 1710, 1665, 1600, 1580 cm$^{-1}$.

(31) 2-[3-(3,4-Dichlorobenzyl)-1,2,3,4-tetrahydro-2,4-dioxoquinazolin-1-yl]acetic acid
mp: 225°-227° C.
IR (Nujol): 1695, 1650, 1600 cm$^{-1}$.

(32) 2-[3-(4-Bromo-2-fluorobenzyl)-1,2,3,4-tetrahydro-2,4-dioxoquinazolin-1-yl]acetic acid
mp: 208°-210° C.
IR (Nujol): 1730, 1700, 1660, 1610 cm$^{-1}$.

(33) 2-[3-Benzyl-1,2,3,4-tetrahydro-2,4-dioxoquinazolin-1-yl]acetic acid
mp: 222°-223° C.
IR (Nujol): 1725, 1700, 1655, 1605, 1480 cm$^{-1}$.

(34) 2-[3-(3,4-Dichlorobenzyl)-1,2,3,4-tetrahydro-2,4-dioxoquinazolin-1-yl]propionic acid
mp: 93° C.
IR (Nujol): 1700, 1655, 1605 cm$^{-1}$.

(35) 2-[3-(3,4-Dichlorobenzyl)-1,2,3,4-tetrahydro-2-oxo-4-thioxoquinazolin-1-yl]acetic acid
mp: 253.5°-254.5° C.
IR (Nujol): 1705, 1680, 1660, 1600, 1585 cm$^{-1}$.

(36) 2-[3-(4-Chlorobenzyl)-1,2,3,4-tetrahydro-2,4-dioxoquinazolin-1-yl]acetic acid
mp: 229°-230° C.
IR (Nujol): 1725, 1705, 1660, 1600, 1480 cm$^{-1}$.

(37) 2-[3-(2,6-Dichlorobenzyl)-1,2,3,4-tetrahydro-2,4-dioxoquinazolin-1-yl]acetic acid
mp: 273°-275° C.
IR (Nujol): 1720, 1660, 1605, 1475 cm$^{-1}$.

(38) 2-[3-(3,5-Dichlorobenzyl)-1,2,3,4-tetrahydro-2,4-dioxoquinazolin-1-yl]acetic acid mp: 212°–213° C.
IR (Nujol): 1740, 1720, 1690, 1635, 1605, 1560, 1480 cm$^{-1}$.

(39) 2-[3-(2,4-Dichlorobenzyl)-1,2,3,4-tetrahydro-2,4-dioxoquinazolin-1-yl]acetic acid
mp: 223° C.
IR (Nujol): 1720, 1675, 1615 cm$^{-1}$.

(40) 2-[3-(2,5-Dichlorobenzyl)-1,2,3,4-tetrahydro-2,4-dioxoquinazolin-1-yl]acetic acid
mp: 207° C.
IR (Nujol): 1710, 1665, 1605 cm$^{-1}$.

(41) 2-[1,2,3,4-Tetrahydro-3-(4-methoxybenzyl)-2,4-dioxoquinazolin-1-yl]acetic acid
mp: 213°–215° C.
IR (Nujol): 1720, 1700, 1660, 1600, 1480 cm$^{-1}$.

(42) 2-[1,2,3,4-Tetrahydro-3-(1-naphthylmethyl)-2,4-dioxoquinazolin-1-yl]acetic acid
mp: 216°–218° C.
IR (Nujol): 1705, 1660, 1605 cm$^{-1}$.

(43) 2-[1,2,3,4-Tetrahydro-2,4-dioxo-3-(2-pyridylmethyl)quinazolin-1-yl]acetic acid
mp: 220°–223° C.
IR (Nujol): 1710, 1660, 1610 cm$^{-1}$.

(44) 2-[3-(4-Bromo-2-fluorobenzyl)-1,2,3,4-tetrahydro-7-methoxy-2,4-dioxoquinazolin-1-yl]acetic acid
mp: 222°–223° C.
IR (Nujol): 1715, 1660, 1620 cm$^{-1}$.

(45) 2-[3-(4-Bromo-2-fluorobenzyl)-1,2,3,4-tetrahydro-6-methoxy-2,4-dioxoquinazolin-1-yl]acetic acid
mp: 224°–226° C.
IR (Nujol): 1740, 1690, 1640, 1500, 1480 cm$^{-1}$.

(46) 2-[3-(4-Bromo-2-fluorobenzyl)-7-chloro-1,2,3,4-tetrahydro-2,4-dioxoquinazolin-1-yl]acetic acid
mp: 223°–224° C.
IR (Nujol): 1720, 1700, 1660, 1600 cm$^{-1}$.

(47) 2-[3-(4-Bromo-2-fluorobenzyl)-6-chloro-1,2,3,4-tetrahydro-2,4-dioxoquinazolin-1-yl]acetic acid
mp: 238°–239° C.
IR (Nujol): 1725, 1710 (sh), 1665, 1605 cm$^{-1}$.

(48) 2-[2-(3,4-Dichlorobenzyl)-3,4-dihydro-3-oxo-2H-1,2,4-benzothiadiazin-4-yl]acetic acid 1,1-dioxide
mp: 190° C.
IR (Nujol): 1720, 1690, 1660 cm$^{-1}$.

(49) 2-[3-(2-Fluoro-4-iodobenzyl)-1,2,3,4-tetrahydro-2,4-dioxoquinazolin-1-yl]acetic acid
mp: 217° C.
IR (Nujol): 1765, 1705, 1645, 1605, 1480 cm$^{-1}$.

(50) 2-[3-(4-Chloro-2-fluorobenzyl)-1,2,3,4-tetrahydro-2,4-dioxoquinazolin-1-yl]acetic acid
mp: 215° C.
IR (Nujol): 1730, 1710, 1665, 1630, 1610, 1480 cm$^{-1}$.

(51) 2-[3-(4-Bromo-3-chlorobenzyl)-1,2,3,4-tetrahydro-2,4-dioxoquinazolin-1-yl]acetic acid
mp: 233°–234° C.
IR (Nujol): 1695, 1680, 1600, 1470 cm$^{-1}$.

(52) 2-[3-(2,3-Dichlorobenzyl)-1,2,3,4-tetrahydro-2,4-dioxoquinazolin-1-yl]acetic acid
mp: 212° C.
IR (Nujol): 1720, 1700, 1660, 1600 cm$^{-1}$.
NMR (DMSO-d$_6$, δ): 4.93 (2H, s), 5.27 (2H, s), 6.83–8.23 (7H, m).

(53) 2-[1,2,3,4-Tetrahydro-3-(4-methylbenzyl)-2,4-dioxoquinazolin-1-yl]acetic acid
mp: 223°–224° C.
IR (Nujol): 1725, 1700, 1655, 1605, 1480 cm$^{-1}$.
NMR (DMSO-d$_6$, δ): 2.27 (3H, s), 4.88 (2H, s), 5.10 (2H, s), 6.97–8.20 (8H, m).

(54) 2-[3-(4-Chloro-3-methoxybenzyl)-1,2,3,4-tetrahydro-2,4-dioxoquinazolin-1-yl]acetic acid
mp: 184° C.
IR (Nujol): 1725, 1700, 1650, 1610 cm$^{-1}$.
NMR (DMSO-d$_6$, δ): 3.81 (3H, s), 4.92 (2H, s), 5.18 (2H, s), 6.78–8.18 (7H, m).

(55) 2-[3-(3-Chloro-4-methoxybenzyl)-1,2,3,4-tetrahydro-2,4-dioxoquinazolin-1-yl]acetic acid
mp: 198° C.
IR (Nujol): 1740, 1695, 1640, 1605 cm$^{-1}$.

(56) 2-[3-(4-Bromo-2-fluorobenzyl)-1,2,3,4-tetrahydro-8-methoxy-2,4-dioxoquinazolin-1-yl]acetic acid
mp: 204°–206° C.
IR (Nujol): 1730, 1700, 1660, 1600 cm$^{-1}$.

(57) 2-[1,2,3,4-Tetrahydro-2,4-dioxo-3-(2-thienylmethyl)quinazolin-1-yl]acetic acid
mp: 248°–250° C. (decomp.).
IR (Nujol): 1725, 1700, 1655, 1605 cm$^{-1}$.

(58) 2-[1,2,3,4-Tetrahydro-3-(2-naphthylmethyl)-2,4-dioxoquinazolin-1-yl]acetic acid
mp: 183°–185° C.

(59) 2-[3-(4-Bromo-2-fluorobenzyl)-5-chloro-1,2,3,4-tetrahydro-2,4-dioxoquinazolin-1-yl]acetic acid
mp: 217°–218° C.
IR (Nujol): 1725, 1710, 1660, 1590 cm$^{-1}$.

(60) 2-[3-(4-Bromo-2-fluorobenzyl)-1,2,3,4-tetrahydro-5-methoxy-2,4-dioxoquinazolin-1-yl]acetic acid
mp: 253°–255° C.
IR (Nujol): 1735, 1700, 1640, 1600 cm$^{-1}$.

EXAMPLE 2

(1) To a suspension of sodium hydride (60% in mineral oil, 367 mg) in N,N-dimethylformamide (15 ml) was added a solution of ethyl 2-(1,2,3,4-tetrahydro-2,4-dioxoquinazolin-1-yl)acetate (2.0 g) in N,N-dimethylformamide (35 ml) with stirring at room temperature under nitrogen atmosphere, and the mixture was stirred at the same temperature for 15 minutes. To this mixture was added 4-chlorobenzyl chloride (1.48 g) with stirring at room temperature and the mixture was stirred at the same temperature for 1 hour. The solvent was evaporated in vacuo to give a residue, which was dissolved in ethyl acetate. The ethyl acetate solution was washed with water and dried. Evaporation of the solvent gave a residue, which was washed with n-hexane to afford ethyl 2-[3-(4-chlorobenzyl)-1,2,3,4-tetrahydro-2,4-dioxoquinazolin-1-yl]acetate (2.55 g).
mp: 137° C.
IR (Nujol): 1730, 1700, 1670, 1605, 1480 cm$^{-1}$.
NMR (DMSO-d$_6$, δ): 1.20 (3H, t, J=7 Hz), 4.20 (2H, q, J=7 Hz), 5.00 (2H, s), 5.13 (2H, s), 7.17–8.23 (8H, m).

The following compounds were obtained in substantially the same manner as that of Example 2-1).

(2) Ethyl 2-[3-(2,6-dichlorobenzyl)-1,2,3,4-tetrahydro-2,4-dioxoquinazolin-1-yl]acetate
mp: 182°–183° C.
IR (Nujol): 1745, 1720, 1680, 1610, 1480 cm$^{-1}$.
NMR (DMSO-d$_6$, δ): 1.17 (3H, t, J=7 Hz), 4.15 (2H, q, J=7 Hz), 4.93 (2H, s), 5.40 (2H, s), 7.17–8.17 (7H, m).

(3) Ethyl 2-[3-(3,5-dichlorobenzyl)-1,2,3,4-tetrahydro-2,4-dioxoquinazolin-1-yl]acetate
mp: 122°–123° C.
IR (Nujol): 1730, 1700, 1660, 1600, 1570, 1480 cm$^{-1}$.
NMR (DMSO-d$_6$, δ): 1.22 (3H, t, J=7 Hz), 4.18 (2H, q, J=7 Hz), 5.00 (2H, s), 5.17 (2H, s), 7.15–8.23 (7H, m).

(4) Ethyl 2-[3-(2,4-dichlorobenzyl)-1,2,3,4-tetrahydro-2,4-dioxoquinazolin-1-yl]acetate
IR (Nujol): 1730, 1710, 1660, 1610 cm$^{-1}$.

NMR (DMSO-d$_6$, δ): 1.20 (3H, t, J=7 Hz), 4.17 (2H, q, J=7 Hz), 5.00 (2H, s), 5.20 (2H, s), 7.02–8.18 (7H, m).

(5) Ethyl 2-[3-(2,5-dichlorobenzyl)-1,2,3,4-tetrahydro-2,4-dioxoquinazolin-1-yl]acetate IR (Nujol): 1740, 1705, 1660, 1605 cm$^{-1}$.

NMR (DMSO-d$_6$, δ): 1.21 (3H, t, J=7 Hz), 4.18 (2H, q, J=7 Hz), 5.00 (2H, s), 5.20 (2H, s), 7.06–8.17 (7H, m).

(6) Ethyl 2-[1,2,3,4-tetrahydro-3-(4-methoxybenzyl)-2,4-dioxoquinazolin-1-yl]acetate mp: 135° C.

IR (Nujol): 1730, 1700, 1660, 1600, 1480 cm$^{-1}$.

NMR (DMSO-d$_6$, δ): 1.20 (3H, t, J=7 Hz), 3.72 (3H, s), 4.23 (2H, q, J=7 Hz), 5.00 (2H, s), 5.10 (2H, s), 6.85 (2H, d, J=9 Hz), 7.30 (2H, d, J=9 Hz), 7.17–8.20 (4H, m).

(7) Ethyl 2-[1,2,3,4-tetrahydro-3-(1-naphthylmethyl)-2,4-dioxoquinazolin-1-yl]acetate mp: 164°–167° C.

IR (Nujol): 1745, 1700, 1660, 1605 cm$^{-1}$.

NMR (CDCl$_3$, δ): 1.25 (3H, t, J=7 Hz), 4.23 (2H, q, J=7 Hz), 4.90 (2H, s), 5.80 (2H, s), 6.90–8.43 (11H, m).

(8) Ethyl 2-[1,2,3,4-tetrahydro-2,4-dioxo-3-(2-pyridylmethyl)quinazolin-1-yl]acetate mp: 141°–143° C.

IR (Nujol): 1740, 1700, 1650, 1610 cm$^{-1}$.

NMR (CDCl$_3$, δ): 1.25 (3H, t, J=7 Hz), 4.23 (2H, q, J=7 Hz), 4.90 (2H, s), 5.43 (2H, s), 6.93–8.67 (8H, m).

(9) Ethyl 2-[3-(4-bromo-2-fluorobenzyl)-1,2,3,4-tetrahydro-7-methoxy-2,4-dioxoquinazolin-1-yl]acetate IR (Nujol): 1740, 1690, 1650, 1610 cm$^{-1}$.

NMR (DMSO-d$_6$, δ): 1.20 (3H, t, J=7 Hz), 3.88 (3H, s), 4.14 (2H, q, J=7 Hz), 4.97 (2H, s), 5.10 (2H, s), 6.83–8.05 (6H, m).

(10) Ethyl 2-[3-(4-bromo-2-fluorobenzyl)-1,2,3,4-tetrahydro-6-methoxy-2,4-dioxoquinazolin-1-yl]acetate mp: 160°–160.5° C.

IR (Nujol): 1725, 1700, 1655, 1500, 1480 cm$^{-1}$.

NMR (DMSO-d$_6$, δ): 1.20 (3H, t, J=7 Hz), 3.88 (3H, s), 4.23 (2H, q, J=7 Hz), 5.00 (2H, s), 5.20 (2H, s), 6.95–7.67 (6H, m).

(11) Ethyl 2-[3-(4-bromo-2-fluorobenzyl)-6-chloro-1,2,3,4-tetrahydro-2,4-dioxoquinazolin-1-yl]acetate mp: 146°–147° C.

IR (Nujol): 1730, 1710, 1675, 1610 cm$^{-1}$.

NMR (CDCl$_3$, δ): 1.27 (3H, t, J=7 Hz), 4.25 (2H, q, J=7 Hz), 4.87 (2H, s), 5.30 (2H, s), 6.87–8.33 (6H, m).

(12) Ethyl 2-[3-(2-fluoro-4-iodobenzyl)-1,2,3,4-tetrahydro-2,4-dioxoquinazolin-1-yl]acetate mp: 157° C.

IR (Nujol): 1750, 1705, 1670, 1610, 1480 cm$^{-1}$.

NMR (DMSO-d$_6$, δ): 1.22 (3H, t, J=7 Hz), 4.18 (2H, q, J=7 Hz), 4.98 (2H, s), 5.15 (2H, s), 6.77–8.20 (7H, m).

(13) Ethyl 2-[3-(4-chloro-2-fluorobenzyl)-1,2,3,4-tetrahydro-2,4-dioxoquinazolin-1-yl]acetate mp: 144°–145° C.

IR (Nujol): 1730, 1705, 1660, 1610, 1480 cm$^{-1}$.

NMR (DMSO-d$_6$, δ): 1.18 (3H, t, J=7 Hz), 4.18 (2H, q, J=7 Hz), 4.97 (2H, s), 5.17 (2H, s), 7.10–8.23 (7H, m).

(14) Ethyl 2-[3-(4-bromo-3-chlorobenzyl)-1,2,3,4-tetrahydro-2,4-dioxoquinazolin-1-yl]acetate mp: 128°–129° C.

IR (Nujol): 1735, 1700, 1660, 1600, 1480 cm$^{-1}$.

NMR (DMSO-d$_6$, δ): 1.22 (3H, t, J=7 Hz), 4.20 (2H, q, J=7 Hz), 5.0 (2H, s), 5.13 (2H, s), 7.10–8.23 (7H, m).

(15) Ethyl 2-[3-(2,3-dichlorobenzyl)-1,2,3,4-tetrahydro-2,4-dioxoquinazolin-1-yl]acetate mp: 158°–160° C.

IR (Nujol): 1740, 1705, 1660, 1605, 1480 cm$^{-1}$.

NMR (DMSO-d$_6$, δ): 1.22 (3H, t, J=7 Hz), 4.20 (2H, q, J=7 Hz), 5.02 (2H, s), 5.25 (2H, s), 6.88–8.22 (7H, m).

(16) Ethyl 2-[1,2,3,4-tetrahydro-3-(4-methylbenzyl)-2,4-dioxoquinazolin-1-yl]acetate mp: 140°–141° C.

IR (Nujol): 1735, 1700, 1660, 1605, 1480 cm$^{-1}$.

NMR (DMSO-d$_6$, δ): 1.20 (3H, t, J=7 Hz), 2.30 (3H, s), 4.25 (2H, q, J=7 Hz), 5.03 (2H, s), 5.17 (2H, s), 7.01–8.30 (8H, m).

(17) Ethyl 2-[3-(4-chloro-3-methoxybenzyl)-1,2,3,4-tetrahydro-2,4-dioxoquinazolin-1-yl]acetate IR (Nujol): 1740, 1705, 1660, 1610 cm$^{-1}$.

NMR (DMSO-d$_6$, δ): 1.20 (3H, t, J=7 Hz), 3.81 (3H, s), 4.16 (2H, q, J=7 Hz), 4.98 (2H, s), 5.13 (2H, s), 6.77–8.13 (7H, m).

(18) Ethyl 2-[3-(3-chloro-4-methoxybenzyl)-1,2,3,4-tetrahydro-2,4-dioxoquinazolin-1-yl]acetate IR (Nujol): 1730, 1700, 1660, 1605 cm$^{-1}$.

NMR (DMSO-d$_6$, δ): 1.21 (3H, t, J=7 Hz), 3.83 (3H, s), 4.21 (2H, q, J=7 Hz), 5.00 (2H, s), 5.08 (2H, s), 6.98–8.18 (7H, m).

(19) Ethyl 2-[1,2,3,4-tetrahydro-2,4-dioxo-3-(2-thienylmethyl)quinazolin-1-yl]acetate mp: 115°–120° C.

IR (Nujol): 1730, 1700, 1660, 1605 cm$^{-1}$.

NMR (CDCl$_3$, δ): 1.25 (3H, t, J=7 Hz), 4.23 (2H, q, J=7 Hz), 4.88 (2H, s), 5.42 (2H, s), 6.82–8.40 (7H, m).

(20) Ethyl 2-[1,2,3,4-tetrahydro-2,4-dioxo-3-(2-naphthylmethyl)quinazolin-1-yl]acetate mp: 149°–150° C.

NMR (CDCl$_3$, δ): 1.23 (3H, t, J=7 Hz), 4.22 (2H, q, J=7 Hz), 4.87 (2H, s), 5.43 (2H, s), 6.87–8.40 (11H, m).

(21) Ethyl 2-[3-(4-bromo-2-fluorobenzyl)-5-chloro-1,2,3,4-tetrahydro-2,4-dioxoquinazolin-1-yl]acetate mp: 186°–187° C.

IR (Nujol): 1740, 1710, 1670, 1590 cm$^{-1}$.

(22) Ethyl 2-[3-(4-bromo-2-fluorobenzyl)-1,2,3,4-tetrahydro-5-methoxy-2,4-dioxoquinazolin-1-yl]acetate mp: 166°–168° C.

IR (Nujol): 1735, 1710, 1665, 1600, 1580 cm$^{-1}$.

(23) Ethyl 2-[3-(3,4-dichlorobenzyl)-1,2,3,4-tetrahydro-2,4-dioxoquinazolin-1-yl]acetate mp: 121°–122° C.

IR (Nujol): 1725, 1700, 1665, 1605 cm$^{-1}$.

(24) Ethyl 2-[3-(4-bromo-2-fluorobenzyl)-1,2,3,4-tetrahydro-2,4-dioxoquinazolin-1-yl]acetate mp: 153°–154° C.

IR (Nujol): 1735, 1715, 1665, 1605 cm$^{-1}$.

(25) Ethyl 2-[3-benzyl-1,2,3,4-tetrahydro-2,4-dioxoquinazolin-1-yl]acetate

IR (Nujol): 1740, 1700, 1660, 1650 cm$^{-1}$.

(26) Ethyl 2-[3-(3,4-dichlorobenzyl)-1,2,3,4-tetrahydro-2,4-dioxoquinazolin-1-yl]propionate mp: 130°–131° C.

IR (Nujol): 1735, 1700, 1655, 1605 cm$^{-1}$.

(27) Ethyl 2-[3-(3,4-dichlorobenzyl)-1,2,3,4-tetrahydro-2-oxo-4-thioxoquinazolin-1-yl]acetate mp: 157°–158° C.

IR (Nujol): 1740, 1690, 1605, 1590 cm$^{-1}$.

(28) Ethyl 2-[2-(3,4-dichlorobenzyl)-3,4-dihydro-3-oxo-2H-1,2,4-benzothiadiazin-4-yl]acetate 1,1-dioxide IR (CHCl$_3$): 1740, 1690, 1600 cm$^{-1}$.

(29) Ethyl 2-[3-(4-bromo-2-fluorobenzyl)-1,2,3,4-tetrahydro-8-methoxy-2,4-dioxoquinazolin-1-yl]acetate IR (Nujol): 1755, 1745, 1700, 1660, 1600 cm$^{-1}$.

EXAMPLE 3

(1) A mixture of ethyl 2-[3-(3,4-dichlorobenzyl)-1,2,3,4-tetrahydro-2,4-dioxoquinazolin-1-yl]acetate (1.2 g) and aqueous 1N sodium hydroxide (3 ml) in methanol (25 ml) was refluxed for 1 hour. After cooling, the solvent was removed under reduced pressure to give a residue, which was acidified with aqueous 1N hydrochloric acid and extracted with ethyl acetate. The extract was washed with brine, dried and evaporated. Thus obtained product was purified by recrystallization from isopropyl ether to give 2-[3-(3,4-dichlorobenzyl)-1,2,3,4-tetrahydro-2,4-dioxoquinazolin-1-yl]acetic acid (1.075 g).

mp: 225°–227° C.
IR (Nujol): 1695, 1650, 1600 cm$^{-1}$.
NMR (DMSO-d$_6$, δ): 4.88 (2H, s), 5.13 (2H, s), 7.17–8.20 (7H, m).

The following compounds were obtained in substantially the same manner as that of Example 3-1).

(2) 2-[3-(4-Bromo-2-fluorobenzyl)-1,2,3,4-tetrahydro-2,4-dioxoquinazolin-1-yl]acetic acid
mp: 208°–210° C.
IR (Nujol): 1730, 1700, 1660, 1610 cm$^{-1}$.
NMR (DMSO-d$_6$, δ): 4.90 (2H, s), 5.17 (2H, s), 6.9–8.1 (7H, m).

(3) 2-[3-Benzyl-1,2,3,4-tetrahydro-2,4-dioxoquinazolin-1-yl]acetic acid
mp: 222°–223° C.
IR (Nujol): 1725, 1700, 1655, 1605, 1480 cm$^{-1}$.
NMR (DMSO-d$_6$, δ): 4.87 (2H, s), 5.15 (2H, s), 7.17–8.23 (9H, m).

(4) 2-[3-(3,4-Dichlorophenyl)-1,2,3,4-tetrahydro-2,4-dioxoquinazolin-1-yl]acetic acid
mp: 268° C.
IR (Nujol): 1730, 1720, 1670, 1640, 1610 cm$^{-1}$.
NMR (DMSO-d$_6$, δ): 4.88 (2H, s), 7.18–8.17 (7H, m).

(5) 2-[3-(3,4-Dichlorobenzyl)-1,2,3,4-tetrahydro-2,4-dioxoquinazolin-1-yl]propionic acid
mp: 93° C.
IR (Nujol): 1700, 1655, 1605 cm$^{-1}$.
NMR (CDCl$_3$, δ): 1.70 (3H, d, J=7 Hz), 5.15 (2H, s), 5.38 (1H, q, J=7 Hz), 7.00–8.37 (7H, m).

(6) 2-[3-(3,4-Dichlorobenzyl)-1,2,3,4-tetrahydro-2-oxo-4-thioxoquinazolin-1-yl]acetic acid
mp: 253.5°–254.5° C.
IR (Nujol): 1705, 1680, 1660, 1600, 1585 cm$^{-1}$.
NMR (DMSO-d$_6$, δ): 4.95 (2H, s), 5.80 (2H, s), 7.20–8.70 (7H, m).

(7) 2-[3-(4-Chlorobenzyl)-1,2,3,4-tetrahydro-2,4-dioxoquinazolin-1-yl]acetic acid
mp: 229°–230° C.
IR (Nujol): 1725, 1705, 1660, 1600, 1480 cm$^{-1}$.
NMR (DMSO-d$_6$, δ): 4.90 (2H, s), 5.13 (2H, s), 7.23–8.23 (8H, m).

(8) 2-[3-(2,6-Dichlorobenzyl)-1,2,3,4-tetrahydro-2,4-dioxoquinazolin-1-yl]acetic acid
mp: 273°–275° C.
IR (Nujol): 1720, 1660, 1605, 1475 cm$^{-1}$.
NMR (DMSO-d$_6$, δ): 4.85 (2H, s), 5.40 (2H, s), 7.07–8.13 (7H, m).

(9) 2-[3-(3,5-Dichlorobenzyl)-1,2,3,4-tetrahydro-2,4-dioxoquinazolin-1-yl]acetic acid
mp: 212°–213° C.
IR (Nujol): 1740, 1720, 1690, 1635, 1605, 1560, 1480 cm$^{-1}$.
NMR (DMSO-d$_6$, δ): 4.88 (2H, s), 5.13 (2H, s), 7.13–8.20 (7H, m).

(10) 2-[3-(2,4-Dichlorobenzyl)-1,2,3,4-tetrahydro-2,4-dioxoquinazolin-1-yl]acetic acid
mp: 223° C.
IR (Nujol): 1720, 1675, 1615 cm$^{-1}$.
NMR (DMSO-d$_6$, δ): 4.90 (2H, s), 5.18 (2H, s), 7.00–8.15 (7H, m).

(11) 2-[3-(2,5-Dichlorobenzyl)-1,2,3,4-tetrahydro-2,4-dioxoquinazolin-1-yl]acetic acid
mp: 207° C.
IR (Nujol): 1710, 1665, 1605 cm$^{-1}$.
NMR (DMSO-d$_6$, δ): 4.90 (2H, s), 5.20 (2H, s), 7.09–8.17 (7H, s).

(12) 2-[1,2,3,4-Tetrahydro-3-(4-methoxybenzyl)-2,4-dioxoquinazolin-1-yl]acetic acid
mp: 213°–215° C.
IR (Nujol): 1720, 1700, 1660, 1600, 1480 cm$^{-1}$.
NMR (DMSO-d$_6$, δ): 3.70 (3H, s), 4.88 (2H, s), 5.08 (2H, s), 6.90 (2H, d, J=6 Hz), 7.30 (2H, d, J=6 Hz), 7.22–8.22 (4H, m).

(13) 2-[1,2,3,4-Tetrahydro-3-(1-naphthylmethyl)-2,4-dioxoquinazolin-1-yl]acetic acid
mp: 216°–218° C.
IR (Nujol): 1705, 1660, 1605 cm$^{-1}$.
NMR (DMSO-d$_6$, δ): 4.93 (2H, s), 5.67 (2H, s), 7.03–8.40 (11H, m), 13.20 (1H, broad s).

(14) 2-[1,2,3,4-Tetrahydro-2,4-dioxo-3-(2-pyridylmethyl)quinazolin-1-yl]acetic acid
mp: 220°–223° C.
IR (Nujol): 1710, 1660, 1610 cm$^{-1}$.
NMR (DMSO-d$_6$, δ): 4.90 (2H, s), 5.27 (2H, s), 7.15–8.55 (8H, m).

(15) 2-[3-(4-Bromo-2-fluorobenzyl)-1,2,3,4-tetrahydro-7-methoxy-2,4-dioxoquinazolin-1-yl]acetic acid
mp: 222°–223° C.
IR (Nujol): 1715, 1660, 1620 cm$^{-1}$.
NMR (DMSO-d$_6$, δ): 3.88 (3H, s), 4.88 (2H, s), 5.12 (2H, s), 6.83–8.07 (6H, m).

(16) 2-[3-(4-Bromo-2-fluorobenzyl)-1,2,3,4-tetrahydro-6-methoxy-2,4-dioxoquinazolin-1-yl]acetic acid
mp: 224°–226° C.
IR (Nujol): 1740, 1690, 1640, 1500, 1480 cm$^{-1}$.
NMR (DMSO-d$_6$, δ): 3.83 (3H, s), 4.87 (2H, s), 5.17 (2H, s), 6.87–7.73 (6H, m).

(17) 2-[3-(4-Bromo-2-fluorobenzyl)-6-chloro-1,2,3,4-tetrahydro-2,4-dioxoquinazolin-1-yl]acetic acid
mp: 238°–239° C.
IR (Nujol): 1725, 1710 (sh), 1665, 1605 cm$^{-1}$.
NMR (DMSO-d$_6$, δ): 4.88 (2H, s), 5.15 (2H, s), 7.05–8.12 (6H, m).

(18) 2-[2-(3,4-Dichlorobenzyl)-3,4-dihydro-3-oxo-2H-1,2,4-benzothiadiazin-4-yl]acetic acid 1,1-dioxide
mp: 190° C.
IR (Nujol): 1720, 1690, 1660 cm$^{-1}$.
NMR (DMSO-d$_6$, δ): 3.98 (2H, s), 4.90 (2H, s), 7.20–8.07 (7H, m).

(19) 2-[3-(2-Fluoro-4-iodobenzyl)-1,2,3,4-tetrahydro-2,4-dioxoquinazolin-1-yl]acetic acid
mp: 217° C.
IR (Nujol): 1765, 1705, 1645, 1605, 1480 cm$^{-1}$.
NMR (DMSO-d$_6$, δ): 4.87 (2H, s), 5.13 (2H, s), 6.77–8.23 (7H, m).

(20) 2-[3-(4-Chloro-2-fluorobenzyl)-1,2,3,4-tetrahydro-2,4-dioxoquinazolin-1-yl]acetic acid
mp: 215° C.
IR (Nujol): 1730, 1710, 1665, 1630, 1610, 1480 cm$^{-1}$.
NMR (DMSO-d$_6$, δ): 4.88 (2H, s), 5.18 (2H, s), 7.12–8.22 (7H, m).

(21) 2-[3-(4-Bromo-3-chlorobenzyl)-1,2,3,4-tetrahydro-2,4-dioxoquinazolin-1-yl]acetic acid
mp: 233°-234° C.
IR (Nujol): 1695, 1680, 1600, 1470 cm$^{-1}$.
NMR (DMSO-d$_6$, δ): 4.93 (2H, s), 5.17 (2H, s), 7.05-8.25 (7H, m).

(22) 2-[3-(2,3-Dichlorobenzyl)-1,2,3,4-tetrahydro-2,4-dioxoquinazolin-1-yl]acetic acid
mp: 212° C.
IR (Nujol): 1720, 1700, 1660, 1600, 1480 cm$^{-1}$.
NMR (DMSO-d$_6$, δ): 4.93 (2H, s), 5.27 (2H, s), 6.83-8.23 (7H, m).

(23) 2-[1,2,3,4-Tetrahydro-3-(4-methylbenzyl)-2,4-dioxoquinazolin-1-yl]acetic acid
mp: 223°-224° C.
IR (Nujol): 1725, 1700, 1655, 1605, 1480 cm$^{-1}$.
NMR (DMSO-d$_6$, δ): 2.27 (3H, s), 4.88 (2H, s), 5.10 (2H, s), 6.97-8.20 (8H, m).

(24) 2-[3-(4-Chloro-3-methoxybenzyl)-1,2,3,4-tetrahydro-2,4-dioxoquinazolin-1-yl]acetic acid
mp: 184° C.
IR (Nujol): 1725, 1700, 1650, 1610 cm$^{-1}$.
NMR (DMSO-d$_6$, δ): 3.81 (3H, s), 4.92 (2H, s), 5.18 (2H, s), 6.78-8.18 (7H, m).

(25) 2-[3-(3-Chloro-4-methoxybenzyl)-1,2,3,4-tetrahydro-2,4-dioxoquinazolin-1-yl]acetic acid
mp: 198° C.
IR (Nujol): 1740, 1695, 1640, 1605 cm$^{-1}$.
NMR (DMSO-d$_6$, δ): 3.83 (3H, s), 4.90 (2H, s), 5.08 (2H, s), 6.99-8.15 (7H, m).

(26) 2-[3-(4-Bromo-2-fluorobenzyl)-1,2,3,4-tetrahydro-8-methoxy-2,4-dioxoquinazolin-1-yl]acetic acid
mp: 204°-206° C.
IR (Nujol): 1730, 1700, 1660, 1600 cm$^{-1}$.
NMR (DMSO-d$_6$, δ): 3.83 (3H, s), 5.00 (2H, s), 5.15 (2H, s), 7.13-7.80 (6H, m).

(27) 2-[1,2,3,4-Tetrahydro-2,4-dioxo-3-(2-thienylmethyl)quinazolin-1-yl]acetic acid
mp: 248°-250° C. (decomp.).
IR (Nujol): 1725, 1700, 1655, 1605 cm$^{-1}$.
NMR (DMSO-d$_6$, δ): 4.88 (2H, s), 5.28 (2H, s), 6.87-8.23 (7H, m), 12.67 (1H, broad s).

(28) 2-[1,2,3,4-Tetrahydro-3-(2-naphthylmethyl)-2,4-dioxoquinazolin-1-yl]acetic acid
mp: 183°-185° C.
NMR (DMSO-d$_6$, δ): 4.92 (2H, s), 5.33 (2H, s), 7.23-8.23 (11H, m).

(29) 2-[3-(4-Bromo-2-fluorobenzyl)-5-chloro-1,2,3,4-tetrahydro-2,4-dioxoquinazolin-1-yl]acetic acid
mp: 217°-218° C.
IR (Nujol): 1725, 1710, 1660, 1590 cm$^{-1}$.

(30) 2-[3-(4-Bromo-2-fluorobenzyl)-1,2,3,4-tetrahydro-5-methoxy-2,4-dioxoquinazolin-1-yl]acetic acid
mp: 253°-255° C.
IR (Nujol): 1735, 1700, 1640, 1600 cm$^{-1}$.
NMR (DMSO-d$_6$, δ): 3.83 (3H, s), 4.83 (2H, s), 5.08 (2H, s), 6.80-7.80 (6H, m).

EXAMPLE 4

To a solution of ethyl 2-(7-chloro-1,2,3,4-tetrahydro-2,4-dioxoquinazolin-1-yl)acetate (176 g) in N,N-dimethylformamide (3.5 l) was added sodium hydride (60% in mineral oil, 32.3 g) at 0° C. and the mixture was stirred at room temperature for 4 hours. To the reaction mixture was added a solution of 4-bromo-2-fluorobenzyl bromide (200 g) in N,N-dimethylformamide (100 ml) below 20° C. over a 20-minute period and the resulting mixture was stirred at room temperature for 1 hour. 3N Aqueous hydrochloric acid (62.2 ml) was added to the mixture below 15° C. and the solvent was evaporated in vacuo. The residue was poured into a mixture of ethyl acetate (3 l) and water (3 l), and the resulting mixture was stirred for 15 minutes. The precipitates were filtered off and the organic layer was separated. The solution was washed with brine, dried over magnesium sulfate and evaporated in vacuo. The residue was crystallized with addition of isopropyl ether and the crystals were collected by filtration and washed with isopropyl ether. The crude crystals and the precipitates were mixed and recrystallized from a mixture of ethyl acetate (0.9 l) and n-hexane (0.9 l) to give ethyl 2-[3-(4-bromo-2-fluorobenzyl)-7-chloro-1,2,3,4-tetrahydro-2,4-dioxoquinazolin-1-yl)acetate (251 g).
IR (Nujol): 1740, 1720, 1680, 1610, 1580 cm$^{-1}$.
NMR (DMSO-d$_6$, δ): 1.20 (3H, t, J=7 Hz), 4.17 (2H, q, J=7 Hz), 4.98 (2H, s), 5.13 (2H, s), 7.07-8.15 (6H, m).

EXAMPLE 5

A mixture of ethyl 2-[3-(4-bromo-2-fluorobenzyl)-7-chloro-1,2,3,4-tetrahydro-2,4-dioxoquinazolin-1-yl]acetate (249 g) and 1N aqueous sodium hydroxide (795 ml) in methanol (1.6 l) was refluxed for 30 minutes with stirring. The solvent was evaporated and the residue was dissolved in hot water (5 l). The aqueous solution was poured into ice-cold 0.5N hydrochloric acid (3 l). The precipitates were collected by filtration and recrystallized from a mixture of ethanol (6 l) and water (3 l) to give 2-[3-(4-bromo-2-fluorobenzyl)-7-chloro-1,2,3,4-tetrahydro-2,4-dioxoquinazolin-1-yl]acetic acid (198 g).
mp: 223°-224° C.
IR (Nujol): 1720, 1700, 1660, 1600 cm$^{-1}$.
NMR (DMSO-d$_6$, δ): 4.88 (2H, s), 5.12 (2H, s), 7.05-8.12 (6H, m).

EXAMPLE 6

(1) A solution of 3-(4-bromo-2-fluorobenzyl)-7-chloro-1,2,3,4-tetrahydro-2,4-dioxoquinazoline (500 mg), ethyl bromoacetate (218 mg) and potassium carbonate (360 mg) in N,N-dimethylformamide (5 ml) was stirred at 30° C. for 30 minutes. The solution was evaporated and the residue was dissolved in ethyl acetate. The solution was washed in turn with 0.5N aqueous hydrochloric acid and water, and then dried over magnesium sulfate. The solvent was removed in vacuo to give a crystalline residue, which was crystallized from a mixture of ethyl acetate and n-hexane to give ethyl 2-[3-(4-bromo-2-fluorobenzyl)-7-chloro-1,2,3,4-tetrahydro-2,4-dioxoquinazolin-1-yl]acetate (550 mg).
IR (Nujol): 1740, 1720, 1680, 1610, 1580 cm$^{-1}$.

The following compound was obtained in substantially the same manner as that of Example 61).

(2) Ethyl 2-[7-fluoro-3-(2-fluoro-4-iodobenzyl)-1,2,3,4-tetrahydro-2,4-dioxoquinazolin-1-yl]acetate
IR (Nujol): 1730, 1710, 1680, 1625, 1600, 1570 cm$^{-1}$.
NMR (DMSO-d$_6$, δ): 1.2 (3H, t, J=7.0 Hz), 4.2 (2H, q, J=7.0 Hz), 5.0 (2H, s), 5.1 (2H, s), 7.0 (1H, dd, J=8, 8 Hz), 7.2 (1H, dd, J=8, 8 Hz), 7.5-7.7 (3H, m), 8.1 (1H, dd, J=6, 8 Hz).

EXAMPLE 7

(1) To a solution of 7-bromo-3-(4-bromo-2-fluorobenzyl)-1,2,3,4-tetrahydro-2,4-dioxoquinazoline 2.80 g) in N,N-dimethylformamide (56 ml) was added sodium hydride (60% in mineral oil, 334 mg) with stirring at 0° C. under an atmosphere of nitrogen and the mixture was stirred at room temperature for 1 hour. To this mixture was added ethyl bromoacetate (0.85 ml) dropwise and the mixture was stirred at room temperature for 2 hours. The solvent was removed under reduced pressure to give a residue, which was poured into water and extracted with ethyl acetate. The extract was washed with water and dried. Removal of the solvent followed by recrystallization from isopropyl ether gave ethyl 2-[7-bromo-3-(4-bromo-2-fluorobenzyl)-1,2,3,4-tetrahydro-2,4-dioxoquinazolin-1-yl]acetate (3.11 g).

mp: 163°–164° C.

IR (Nujol): 1740, 1710, 1675, 1600, 1580, 1490 cm$^{-1}$.

NMR (DMSO-$d_6$, δ): 1.20 (3H, t, J=7 Hz), 4.16 (2H, q, J=7 Hz), 4.98 (2H, s), 5.13 (2H, s), 7.14 (1H, dd, J=8, 8 Hz), 7.35 (1H, d, J=8 Hz), 7.52–7.57 (2H, m), 7.83 (1H, s), 7.99 (1H, d, J=8 Hz).

The following compounds were obtained in substantially the same manner as that of Example 7-1).

(2) Ethyl 2-[3-(4-bromo-2-fluorobenzyl)-8-chloro-1,2,3,4-tetrahydro-2,4-dioxoquinazolin-1-yl]acetate mp: 83°–85° C.

IR (Nujol): 1735, 1710, 1660, 1595 cm$^{-1}$.

NMR (CDCl$_3$, δ): 1.25 (3H, t, J=7 Hz), 4.25 (2H, q, J=7 Hz), 5.25 (2H, s), 5.27 (2H, s), 7.10–8.33 (6H, m).

(3) Ethyl 2-[7-chloro-3-{4-chloro-3-(trifluoromethyl)benzyl}-1,2,3,4-tetrahydro-2,4-dioxoquinazolin-1-yl]acetate mp: 133°–134° C.

IR (Nujol): 1730, 1700, 1650, 1600 cm$^{-1}$.

NMR (DMSO-$d_6$, δ): 1.20 (3H, t, J=7 Hz), 4.20 (2H, q, J=7 Hz), 4.98 (2H, s), 5.18 (2H, s), 7.23–8.20 (6H, m).

(4) Ethyl 2-[3-(4-bromo-2-fluorobenzyl)-1,2,3,4-tetrahydro-7-iodo-2,4-dioxoquinazolin-1-yl]acetate mp: 169°–169.5° C.

IR (Nujol): 1740, 1710, 1675, 1595, 1575, 1490 cm$^{-1}$.

NMR (DMSO-$d_6$, δ): 1.20 (3H, t, J=7 Hz), 4.17 (2H, q, J=7 Hz), 4.97 (2H, s), 5.12 (2H, s), 7.13 (1H, dd, J=8, 8 Hz), 7.34 (1H, d, J=8 Hz), 7.55 (1H, d, J=8 Hz), 7.75 (2H, m), 7.92 (1H, s).

(5) Ethyl 2-[3-(4-bromo-2-fluorobenzyl)-7-fluoro-1,2,3,4-tetrahydro-2,4-dioxoquinazolin-1-yl]acetate mp: 144°–145° C.

IR (Nujol): 1700, 1660, 1600, 1370 cm$^{-1}$.

NMR (DMSO-$d_6$, δ): 1.20 (3H, t, J=7 Hz), 4.16 (2H, q, J=7 Hz), 4.96 (2H, s), 5.14 (2H, s), 7.10–7.58 (5H, m), 8.16 (1H, dd, J=7, 7 Hz)

(6) Ethyl 2-[3-(4-bromo-2-fluorobenzyl)-7-trifluoromethyl-1,2,3,4-tetrahydro-2,4-dioxoquinazolin-1-yl]acetate mp: 150°–152° C.

IR (Nujol): 1700, 1660, 1600, 1370, 1260 cm$^{-1}$.

(7) Ethyl 2-[7-bromo-3-(2-fluoro-4-iodobenzyl)-1,2,3,4-tetrahydro-2,4-dioxoquinazolin-1-yl]acetate mp: 183°–184° C.

IR (Nujol): 1735, 1710, 1670 cm$^{-1}$.

NMR (DMSO-$d_6$, δ): 1.20 (3H, t, J=7 Hz), 4.17 (2H, q, J=7 Hz), 4.98 (2H, s), 5.11 (2H, s), 6.96 (1H, t, J=8 Hz), 7.51 (2H, t, J=8 Hz), 7.64 (1H, d, J=10 Hz), 7.82 (1H, s), 7.99 (1H, d, J=8 Hz).

(8) Ethyl 2-[3-(2-fluoro-4-iodobenzyl)-7-iodo-1,2,3,4-tetrahydro-2,4-dioxoquinazolin-1-yl]acetate mp: 184°–185° C.

IR (Nujol): 1740, 1715, 1670, 1600, 720 cm$^{-1}$.

NMR (DMSO-$d_6$, δ): 1.2 (3H, t, J=7 Hz), 4.2 (2H, q, J=7 Hz), 5.0 (2H, s), 5.1 (2H, s), 7.0 (1H, t, J=8 Hz), 7.5–8.3 (5H, m).

(9) Ethyl 2-[3-(4-bromo-2-fluorobenzyl)-6,7-dichloro-1,2,3,4-tetrahydro-2,4-dioxoquinazolin-1-yl]acetate IR (Nujol): 1730, 1710, 1675, 1575, 1490 cm$^{-1}$.

(10) Ethyl 2-[3-(4-bromo-2-fluorobenzyl)-5,7-dichloro-1,2,3,4-tetrahydro-2,4-dioxoquinazolin-1-yl]acetate IR (Nujol): 1730, 1720, 1680, 1595, 1570 cm$^{-1}$.

(11) Ethyl 2-[7-chloro-3-(2-fluoro-4-iodobenzyl)-1,2,3,4-tetrahydro-2,4-dioxoquinazolin-1-yl]acetate IR (Nujol): 1740, 1715, 1675, 1610 cm$^{-1}$.

(12) Ethyl 2-[7-chloro-3-(2-fluoro-3-iodobenzyl)-1,2,3,4-tetrahydro-2,4-dioxoquinazolin-1-yl]acetate IR (Nujol): 1750, 1720, 1660, 1610 cm$^{-1}$.

(13) Ethyl 2-[7-chloro-3-(3-chloro-4-iodobenzyl)-1,2,3,4-tetrahydro-2,4-dioxoquinazolin-1-yl]acetate IR (Nujol): 1735, 1710, 1670, 1605, 1580 cm$^{-1}$.

(14) Ethyl 2-[7-chloro-3-{3,5-bis(trifluoromethyl)benzyl}-1,2,3,4-tetrahydro-2,4-dioxoquinazolin-1-yl]acetate IR (Nujol): 1735, 1710, 1665, 1610, 1580 cm$^{-1}$.

(15) Ethyl 2-[6,7-dichloro-3-(2-fluoro-4-iodobenzyl)-1,2,3,4-tetrahydro-2,4-dioxoquinazolin-1-yl]acetate mp: 225°–226° C.

IR (Nujol): 1725, 1710, 1675, 1605, 1575 cm$^{-1}$.

(16) Sodium 2-[3-(4-bromo-2-fluorobenzyl)-7-chloro-1,2,3,4,-tetrahydro-2,4-dioxoquinazolin-1-yl]acetate mp: >300° C.

IR (Nujol): 3500, 1705, 1670, 1610 cm$^{-1}$.

(17) 2-[7-Bromo-3-(4-bromo-2-fluorobenzyl)-1,2,3,4-tetrahydro-2,4-dioxoquinazolin-1-yl]acetic acid IR (Nujol): 1725, 1710, 1660, 1600, 1580, 1490 cm$^{-1}$.

(18) 2-[3-(4-Bromo-2-fluorobenzyl)-1,2,3,4-tetrahydro-7-iodo-2,4-dioxoquinazolin-1-yl]acetic acid IR (Nujol): 1710, 1670, 1600, 1580, 1490 cm$^{-1}$.

(19) 2-[3-(4-Bromo-2-fluorobenzyl)-7-fluoro-1,2,3,4-tetrahydro-2,4-dioxoquinazolin-1-yl]acetic acid IR (Nujol): 1710, 1660, 1580, 1360 cm$^{-1}$.

(20) 2-[7-Chloro-3-(2-fluoro-4-iodobenzyl)-1,2,3,4-tetrahydro-2,4-dioxoquinazolin-1-yl]acetic acid IR (Nujol): 1730, 1710, 1670, 1610 cm$^{-1}$.

(21) 2-[7-Chloro-3-(2-fluoro-3-iodobenzyl)-1,2,3,4-tetrahydro-2,4-dioxoquinazolin-1-yl]acetic acid IR (Nujol): 1720, 1700, 1660, 1600 cm$^{-1}$.

(22) 2-[7-Chloro-3-(3-chloro-4-iodobenzyl)-1,2,3,4-tetrahydro-2,4-dioxoquinazolin-1-yl]acetic acid IR (Nujol): 1725, 1710, 1665, 1605, 1580 cm$^{-1}$.

(23) 2-[7-Chloro-3-{4-chloro-3-(trifluoromethyl)benzyl}-1,2,3,4-tetrahydro-2,4-dioxoquinazolin-1-yl]acetic acid IR (Nujol): 1720, 1705, 1660, 1600, 1575 cm$^{-1}$.

(24) 2-[7-Chloro-{3,5-bis(trifluoromethyl)benzyl}-1,2,3,4-tetrahydro-2,4-dioxoquinazolin-1-yl]acetic acid IR (Nujol): 1740, 1700, 1650, 1605, 1590 cm$^{-1}$.

(25) 2-[4-Bromo-2-fluorobenzyl)-8-chloro-1,2,3,4-tetrahydro-2,4-dioxoquinazolin-1-yl]acetic acid IR (Nujol): 1730, 1710, 1670, 1605 (sh), 1595 cm$^{-1}$.

(26) 2-[3-(4-Bromo-2-fluorobenzyl)-6,7-dichloro-1,2,3,4-tetrahydro-2,4-dioxoquinazolin-1-yl]acetic acid IR (Nujol): 1720, 1675, 1600, 1570, 1485 cm$^{-1}$.

(27) 2-[3-(4-Bromo-2-fluorobenzyl)-5,7-dichloro-1,2,3,4-tetrahydro-2,4-dioxoquinazolin-1-yl]acetic acid IR (Nujol): 3250, 1730, 1710, 1670, 1665 (sh), 1605, 1590, 1570 cm$^{-1}$.

(28) 2-[3-(4-Bromo-2-fluorobenzyl)-7-trifluoromethyl-1,2,3,4-tetrahydro-2,4-dioxoquinazolin-1-yl]acetic acid IR (Nujol): 1700, 1660, 1580, 1360 cm$^{-1}$.

(29) 2-[6,7-Dichloro-3-(2-fluoro-4-iodobenzyl)-1,2,3,4-tetrahydro-2,4-dioxoquinazolin-1-yl]acetic acid mp: 255°–257° C.

IR (Nujol): 1725 (sh), 1710, 1675, 1600, 1570 cm$^{-1}$.

(30) 2-[7-Bromo-3-(2-fluoro-4-iodobenzyl)-1,2,3,4-tetrahydro-2,4-dioxoquinazolin-1-yl]acetic acid
mp: 252°–253° C.
IR (Nujol): 1715, 1675, 1600 cm$^{-1}$.

(31) 2-[7-Fluoro-3-(2-fluoro-4-iodobenzyl)-1,2,3,4-tetrahydro-2,4-dioxoquinazolin-1-yl]acetic acid
mp: 214°–215° C.
IR (Nujol): 3480, 1710, 1660, 1620, 1600 cm$^{-1}$.

(32) 2-[3-(2-Fluoro-4-iodobenzyl)-7-iodo-1,2,3,4-tetrahydro-2,4-dioxoquinazolin-1-yl]acetic acid
mp: 279°–281° C.
IR (Nujol): 1715, 1680, 1600, 1340, 1260, 840 cm$^{-1}$.

(33) 2-(3-Benzyl-1,2,3,4-tetrahydro-4-oxo-2-thioxoquinazolin-1-yl)acetic acid
mp: 194°–197° C.
IR (Nujol): 1720, 1700 cm$^{-1}$.

(34) 2-[3-(3,4-Dichlorobenzyl)-1,2,3,4-tetrahydro-4-oxo-2-thioxoquinazolin-1-yl]acetic acid
mp: 105°–110° C.
IR (CHCl$_3$): 1700 cm$^{-1}$.

(35) Ethyl 2-[3-(3,4-dichlorobenzyl)-1,2,3,4-tetrahydro-2,4-dithioxoquinazolin-1-yl]acetate
mp: 155°–156° C.
IR (Nujol): 1725 cm$^{-1}$.

(36) 2-[3-(3,4-Dichlorobenzyl)-1,2,3,4-tetrahydro-2,4-dithioxoquinazolin-1-yl]acetic acid
mp: 222°–223° C. (dec.).
IR (Nujol): 1710, 1685 cm$^{-1}$.

EXAMPLE 8

(1) To a suspension of ethyl 2-(6,7-dichloro-1,2,3,4-tetrahydro-2,4-dioxoquinazolin-1-yl)acetate (2.0 g) in N,N-dimethylformamide (50 ml) was added sodium hydride (60% in mineral oil, 288 mg) at room temperature with stirring and the mixture was stirred at the same temperature for 1 hour. To this mixture was added 4-bromo-2-fluorobenzyl bromide (1.93 g) at room temperature with stirring and the mixture was stirred at the same temperature for 2 hours. The solvent was removed to give a residue, which was poured into water. The resulting precipitates were collected by filtration and washed with n-hexane to give ethyl 2-[3-(4-bromo-2-fluorobenzyl)-6,7-dichloro-1,2,3,4-tetrahydro-2,4-dioxoquinazolin-1-yl]acetate (2.94 g).
mp: 220°–221° C.
IR (Nujol): 1730, 1710, 1675, 1575, 1490 cm$^{-1}$.
NMR (DMSO-d$_6$, δ): 1.20 (3H, t, J=7 Hz), 4.16 (2H, q, J=7 Hz), 4.97 (2H, s), 5.12 (2H, s), 7.16 (1H, dd, J=8, 8 Hz), 7.34 (1H, d, J=8 Hz), 7.55 (1H, d, J=8 Hz), 7.97 (1H, s), 8.19 (1H, s).

The following compounds were obtained in substantially the same manner as that of Example 8-1).

(2) Ethyl 2-[3-(4-bromo-2-fluorobenzyl)-5,7-dichloro-1,2,3,4-tetrahydro-2,4-dioxoquinazolin-1-yl]acetate
mp: 172°–173° C.
IR (Nujol): 1730, 1720, 1680, 1595, 1570 cm$^{-1}$.
NMR (CDCl$_3$, δ): 1.30 (3H, t, J=7 Hz), 4.28 (2H, q, J=7 Hz), 4.86 (2H, s), 5.26 (2H, s), 6.87–7.33 (5H, m).

(3) Ethyl 2-[7-chloro-3-(2-fluoro-4-iodobenzyl)-1,2,3,4-tetrahydro-2,4-dioxoquinazolin-1-yl]acetate
mp: 178°–179° C.
IR (Nujol): 1740, 1715, 1675, 1610 cm$^{-1}$.
NMR (CDCl$_3$, δ): 1.29 (3H, t, J=7 Hz), 4.27 (2H, q, J=7 Hz), 4.85 (2H, s), 5.28 (2H, s), 6.97–8.20 (6H, m).

(4) Ethyl 2-[7-chloro-3-(2-fluoro-3-iodobenzyl)-1,2,3,4-tetrahydro-2,4-dioxoquinazolin-1-yl]acetate
mp: 140°–141° C.
IR (Nujol): 1750, 1720, 1660, 1610 cm$^{-1}$.

(5) Ethyl 2-[7-chloro-3-(3-chloro-4-iodobenzyl)-1,2,3,4-tetrahydro-2,4-dioxoquinazolin-1-yl]acetate
mp: 144°–145° C.
IR (Nujol): 1735, 1710, 1670, 1605, 1580 cm$^{-1}$.

(6) Ethyl 2-[7-chloro-3-{3,5-bis(trifluoromethyl)benzyl}-1,2,3,4-tetrahydro-2,4-dioxoquinazolin-1-yl]acetate
mp: 111°–112° C.
IR (Nujol): 1735, 1710, 1665, 1610, 1580 cm$^{-1}$.

(7) Ethyl 2-[6,7-dichloro-3-(2-fluoro-4-iodobenzyl)-1,2,3,4-tetrahydro-2,4-dioxoquinazolin-1-yl]acetate
mp: 225°–226° C.
IR (Nujol): 1725, 1710, 1675, 1605, 1575 cm$^{-1}$.
NMR (DMSO-d$_6$, δ): 1.19 (3H, t, J=7 Hz), 4.16 (2H, q, J=7 Hz), 4.97 (2H, s), 5.11 (2H, s), 6.90–7.75 (3H, m), 7.96 (1H, s), 8.19 (1H, s).

(8) Ethyl 2-[7-bromo-3-(4-bromo-2-fluorobenzyl)-1,2,3,4-tetrahydro-2,4-dioxoquinazolin-1-yl]acetate
IR (Nujol): 1740, 1710, 1675, 1600, 1580, 1490 cm$^{-1}$.

(9) Ethyl 2-[3-(4-bromo-2-fluorobenzyl)-8-chloro-1,2,3,4-tetrahydro-2,4-dioxoquinazolin-1-yl]acetate
IR (Nujol): 1735, 1710, 1660, 1595 cm$^{-1}$.

(10) Ethyl 2-[7-chloro-3-{4-chloro-3-(trifluoromethyl)benzyl}-1,2,3,4-tetrahydro-2,4-dioxoquinazolin-1-yl]acetate
IR (Nujol): 1730, 1700, 1650, 1600 cm$^{-1}$.

(11) Ethyl 2-[3-(4-bromo-2-fluorobenzyl)-1,2,3,4-tetrahydro-7-iodo-2,4-dioxoquinazolin-1-yl]acetate
IR (Nujol): 1740, 1710, 1675, 1595, 1575, 1490 cm$^{-1}$.

(12) Ethyl 2-[3-(4-bromo-2-fluorobenzyl)-7-fluoro-1,2,3,4-tetrahydro-2,4-dioxoquinazolin-1-yl]acetate
IR (Nujol): 1700, 1660, 1600, 1370 cm$^{-1}$.

(13) Ethyl 2-[3-(4-bromo-2-fluorobenzyl)-7-trifluoromethyl-1,2,3,4-tetrahydro-2,4-dioxoquinazolin-1-yl]acetate
IR (Nujol): 1700, 1660, 1600, 1370, 1260 cm$^{-1}$.

(14) Ethyl 2-[7-fluoro-3-(2-fluoro-4-iodobenzyl)-1,2,3,4-tetrahydro-2,4-dioxoquinazolin-1-yl]acetate
IR (Nujol): 1730, 1710, 1680, 1625, 1600, 1570 cm$^{-1}$.

(15) Ethyl 2-[7-bromo-3-(2-fluoro-4-iodobenzyl)-1,2,3,4-tetrahydro-2,4-dioxoquinazolin-1-yl]acetate
mp: 183°–184° C.
IR (Nujol): 1735, 1710, 1670 cm$^{-1}$.

(16) Ethyl 2-[3-(2-fluoro-4-iodobenzyl)-7-iodo-1,2,3,4-tetrahydro-2,4-dioxoquinazolin-1-yl]acetate
mp: 184°–185° C.
IR (Nujol): 1740, 1715, 1670, 1600, 720 cm$^{-1}$.

(17) Ethyl 2-[3-(3,4-dichlorobenzyl)-1,2,3,4-tetrahydro-2,4-dithioxoquinazolin-1-yl]acetate
mp: 155°–156° C.
IR (Nujol): 1725 cm$^{-1}$.

EXAMPLE 9

A solution of ethyl 2-[3-(4-bromo-2-fluorobenzyl)-7-chloro-1,2,3,4-tetrahydro-2,4-dioxoquinazolin-1-yl]acetate (69 g) and 1N aqueous sodium hydroxide (191 ml) in ethanol (350 ml) was stirred at 60° C. for 3 hours. After cooling to 0° C., the precipitates were collected by filtration, washed with water, and dried over phosphorus pentoxide. Recrystallization from water (360 ml) gave sodium 2-[3-(4-bromo-2-fluorobenzyl)-7-chloro-1,2,3,4-tetrahydro-2,4-dioxoquinazolin-1-yl]acetate (39.2 g).
mp: >300° C.
IR (Nujol): 3500, 1705, 1670, 1610 cm$^{-1}$.
NMR (D$_2$O, δ): 4.66 (2H, s), 5.21 (2H, s), 7.1–7.4 (6H, m), 8.04 (1H, d, J=9 Hz).

EXAMPLE 10

(1) A solution of ethyl 2-[7-bromo-3-(4-bromo-2-fluorobenzyl)-1,2,3,4-tetrahydro-2,4-dioxoquinazolin-1-yl]acetate (3.0 g) and 1N aqueous sodium hydroxide (5.83 ml) in methanol (69.6 ml) was refluxed for 1 hour with stirring. After cooling, the solvent was evaporated to give a residue, which was acidified with 1N aqueous hydrochloric acid and extracted with ethyl acetate. The extract was washed with brine and dried. Removal of the solvent gave a residue, which was recrystallized from a mixture of ethyl acetate and n-hexane to afford 2-[7-bromo-3-(4-bromo-2-fluorobenzyl)-1,2,3,4-tetrahydro-2,4-dioxoquinazolin-1-yl]acetic acid (2.36 g).

mp: 217° C.
IR (Nujol): 1725, 1710, 1660, 1600, 1580, 1490 cm$^{-1}$.
NMR (DMSO-d$_6$, δ): 4.90 (2H, s), 5.13 (2H, s), 7.14 (1H, dd, J=8, 8 Hz), 7.34 (1H, d, J=8 Hz), 7.50–7.58 (2H, m), 7.78 (1H, s), 7.99 (1H, d, J=8 Hz).

The following compounds were obtained in substantially the same manner as that of Example 10-1).

(2) 2-[3-(4-Bromo-2-fluorobenzyl)-1,2,3,4-tetrahydro-7-iodo-2,4-dioxoquinazolin-1-yl]acetic acid.
mp: 251°–252.5° C.
IR (Nujol): 1710, 1670, 1600, 1580, 1490 cm$^{-1}$.
NMR (DMSO-d$_6$, δ): 4.89 (2H, s), 5.13 (2H, s), 7.13 (1H, dd, J=8, 8 Hz), 7.34 (1H, d, J=8 Hz), 7.55 (1H, d, J=8 Hz), 7.75 (2H, m), 7.89 (1H, s).

(3) 2-[3-(4-Bromo-2-fluorobenzyl)-7-fluoro-1,2,3,4-tetrahydro-2,4-dioxoquinazolin-1-yl]acetic acid
mp: 210°–211° C.
IR (Nujol): 1710, 1660, 1580, 1360 cm$^{-1}$.
NMR (DMSO-d$_6$, δ): 3.50 (1H, br s), 4.87 (2H, s), 5.14 (2H, s), 7.10–7.56 (5H, m), 8.15 (1H, dd, J=6.6, 7.5 Hz).

(4) 2-[7-Chloro-3-(2-fluoro-4-iodobenzyl)-1,2,3,4-tetrahydro-2,4-dioxoquinazolin-1-yl]acetic acid
mp: 232°–233° C.
IR (Nujol): 1730, 1710, 1670, 1610 cm$^{-1}$.
NMR (DMSO-d$_6$, δ): 4.90 (2H, s), 5.12 (2H, s), 6.93–8.10 (6H, m).

(5) 2-[7-Chloro-3-(2-fluoro-3-iodobenzyl)-1,2,3,4-tetrahydro-2,4-dioxoquinazolin-1-yl]acetic acid
mp: 165°–167° C.
IR (Nujol): 1720, 1700, 1660, 1600 cm$^{-1}$.

(6) 2-[7-Chloro-3-(3-chloro-4-iodobenzyl)-1,2,3,4-tetrahydro-2,4-dioxoquinazolin-1-yl]acetic acid
mp: 240° C.
IR (Nujol): 1725, 1710, 1665, 1605, 1580 cm$^{-1}$.

(7) 2-[7-Chloro-3-{4-chloro-3-(trifluoromethyl)benzyl}-1,2,3,4-tetrahydro-2,4-dioxoquinazolin-1-yl]acetic acid
mp: 212°–213° C.
IR (Nujol): 1720, 1705, 1660, 1600, 1575 cm$^{-1}$.

(8) 2-[7-Chloro-3-{3,5-bis(trifluoromethyl)benzyl}-1,2,3,4-tetrahydro-2,4-dioxoquinazolin-1-yl]acetic acid
mp: 202°–203° C.
IR (Nujol): 1740, 1700, 1650, 1605, 1590 cm$^{-1}$.

(9) 2-[3-(4-Bromo-2-fluorobenzyl)-8-chloro-1,2,3,4-tetrahydro-2,4-dioxoquinazolin-1-yl]acetic acid
mp: 212°–215° C.
IR (Nujol): 1730, 1710, 1670, 1605 (sh), 1595 cm$^{-1}$.
NMR (DMSO-d$_6$, δ): 5.03 (2H, s), 5.12 (2H, s), 7.10–8.23 (6H, m).

(10) 2-[3-(4-Bromo-2-fluorobenzyl)-6,7-dichloro-1,2,3,4-tetrahydro-2,4-dioxoquinazolin-1-yl]acetic acid
mp: 255° C.
IR (Nujol): 1720, 1675, 1600, 1570, 1485 cm$^{-1}$.
NMR (DMSO-d$_6$, δ): 4.90 (2H, s), 5.13 (2H, s), 7.17 (1H, dd, J=8, 8 Hz), 7.34 (1H, d, J=8 Hz), 7.55 (1H, d, J=8 Hz), 7.93 (1H, s), 8.19 (1H, s).

(11) 2-[3-(4-Bromo-2-fluorobenzyl)-5,7-dichloro-1,2,3,4-tetrahydro-2,4-dioxoquinazolin-1-yl]acetic acid
mp: 238°–239° C.
IR (Nujol): 3250, 1730, 1710, 1670, 1665 (sh), 1605, 1590, 1570 cm$^{-1}$.
NMR (DMSO-d$_6$, δ): 4.92 (2H, s), 5.10 (2H, s), 7.13–7.63 (5H, m).

(12) 2-[3-(4-Bromo-2-fluorobenzyl)-7-trifluoromethyl-1,2,3,4-tetrahydro-2,4-dioxoquinazolin-1-yl]acetic acid
mp: 230°–231° C.
IR (Nujol): 1700, 1660, 1580, 1360 cm$^{-1}$.

(13) 2-[6,7-Dichloro-3-(2-fluoro-4-iodobenzyl)-1,2,3,4-tetrahydro-2,4-dioxoquinazolin-1-yl]acetic acid
mp: 255°–257° C.
IR (Nujol): 1725 (sh), 1710, 1675, 1600, 1570 cm$^{-1}$.
NMR (DMSO-d$_6$, δ): 4.90 (2H, s), 5.12 (2H, s), 6.90–7.70 (3H, m), 7.93 (1H, s), 8.18 (1H, s), 13.30 (1H, br s).

(14) 2-[7-Bromo-3-(2-fluoro-4-iodobenzyl)-1,2,3,4-tetrahydro-2,4-dioxoquinazolin-1-yl]acetic acid
mp: 252°–253° C.
IR (Nujol): 1715, 1675, 1600 cm$^{-1}$.
NMR (DMSO-d$_6$, δ): 4.90 (2H, s), 5.12 (2H, s), 6.96 (1H, t, J=8 Hz), 7.50 (2H, t, J=8 Hz), 7.64 (1H, d, J=10 Hz), 7.78 (1H, s), 7.98 (1H, d, J=8 Hz).

(15) 2-[7-Fluoro-3-(2-fluoro-4-iodobenzyl)-1,2,3,4-tetrahydro-2,4-dioxoquinazolin-1-yl]acetic acid
mp: 214°–215° C.
IR (Nujol): 3480, 1710, 1660, 1620, 1600 cm$^{-1}$.
NMR (DMSO-d$_6$, δ): 4.9 (2H, s), 5.1 (2H, s), 7.0 (1H, dd, J=8, 8 Hz), 7.2 (1H, dd, J=8, 8 Hz), 7.4–7.7 (3H, m), 8.1 (1H, dd, J=7, 8 Hz).

(16) 2-[3-(2-Fluoro-4-iodobenzyl)-7-iodo-1,2,3,4-tetrahydro-2,4-dioxoquinazolin-1-yl]acetic acid
mp: 279°–281° C.
IR (Nujol): 1715, 1680, 1600, 1340, 1260, 840 cm$^{-1}$.
NMR (DMSO-d$_6$, δ): 4.90 (2H, s), 5.12 (2H, s), 6.96 (1H, t, J=8 Hz), 7.46–7.89 (5H, m).

EXAMPLE 11

(1) A mixture of ethyl 2-[2-(N-benzylcarbamoyl)anilino]acetate (1.5 g) and N,N'-thiocarbonyldiimidazole (2.85 g) was stirred at 120° C. for 30 minutes. After cooling, the reaction mixture was diluted with chloroform and chromatographed on silica gel. Elution with chloroform gave ethyl 2-(3-benzyl-1,2,3,4-tetrahydro-4-oxo-2-thioxoquinazolin-1-yl)acetate. A mixture of ethyl 2-(3-benzyl-1,2,3,4-tetrahydro-4-oxo-2-thioxoquinazolin-1-yl)acetate and 1N sodium hydroxide (2 ml) in methanol (10 ml) was stirred for 4 hours at room temperature. The reaction mixture was poured into dilute hydrochloric acid and extracted with chloroform. The extract was washed with brine and dried. Removal of the solvent gave 2-(3-benzyl-1,2,3,4-tetrahydro-4-oxo-2-thioxoquinazolin-1-yl)acetic acid (280 mg).

mp: 194°–197° C.
IR (Nujol): 1720, 1700 cm$^{-1}$.
NMR (CD$_3$OD, δ): 4.90 (2H, s), 5.20 (2H, s), 7.00–7.50 (9H, m).

The following compound was obtained in substantially the same manner as that of Example 11-1).

(2) 2-[3-(3,4-Dichlorobenzyl)-1,2,3,4-tetrahydro-4-oxo-2-thioxoquinazolin-1-yl]acetic acid mp: 105°-110° C.
IR (CHCl₃): 1700 cm⁻¹.

EXAMPLE 12

(1) A mixture of ethyl 2-[2-{N-(3,4-dichlorobenzyl)-thiocarbamoyl}anilino]acetate (4.0 g) and N,N'-thiocarbonyldiimidazole (8.97 g) was heated at 120° C. for 15 minutes, and the reaction mixture was chromatographed on silica gel (100 g) eluting with chloroform. The fractions containing the desired compound were combined and concentrated in vacuo. The residue was recrystallized from a mixture of ethyl acetate and hexane to give ethyl 2-[3-(3,4-dichlorobenzyl)-1,2,3,4-tetrahydro-2,4-dithioxoquinazolin-1-yl]acetate (560 mg).
mp: 155°-156° C.
IR (Nujol): 1725 cm⁻¹.
NMR (CDCl₃, δ): 1.31 (3H, t, J=7 Hz), 4.30 (2H, q, J=7 Hz), 5.55 (2H, br s), 6.53 (2H, s), 7.06-7.39 (5H, m), 7.71 (1H, dt, J=1.5, 8 Hz), 8.71 (1H, dd, J=1.5, 8 Hz).

The following compounds were obtained in substantially the same manner as that of Example 12-1).

(2) Ethyl 2-[3-(3,4-dichlorobenzyl)-1,2,3,4-tetrahydro-2,4-dioxoquinazolin-1-yl]acetate
mp: 121°-122° C.
IR (Nujol): 1725, 1700, 1665, 1605 cm⁻¹.

(3) Ethyl 2-[3-(4-bromo-2-fluorobenzyl)-1,2,3,4-tetrahydro-2,4-dioxoquinazolin-1-yl]acetate
mp: 153°-154° C.
IR (Nujol): 1735, 1715, 1665, 1605 cm⁻¹.

(4) Ethyl 2-[3-benzyl-1,2,3,4-tetrahydro-2,4-dioxoquinazolin-1-yl]acetate
IR (Nujol): 1740, 1700, 1660, 1650 cm⁻¹.

(5) Ethyl 2-[3-(3,4-dichlorophenyl)-1,2,3,4-tetrahydro-2,4-dioxoquinazolin-1-yl]acetate
IR (Nujol): 1740, 1710, 1665, 1605 cm⁻¹.

(6) Ethyl 2-[3-(3,4-dichlorobenzyl)-1,2,3,4-tetrahydro-2,4-dioxoquinazolin-1-yl]propionate
mp: 130°-131° C.
IR (Nujol): 1735, 1700, 1655, 1605 cm⁻¹.

(7) Ethyl 2-[3-(3,4-dicholorobenzyl)-1,2,3,4-tetrahydro-2-oxo-4-thioxoquinazolin-1-yl]acetate
mp: 157°-158° C.
IR (Nujol): 1740, 1690, 1605, 1590 cm⁻¹.

(8) Ethyl 2-[2-(3,4-dichlorobenzyl)-3,4-dihydro-3-oxo-2H-1,2,4-benzothiadiazin-4-yl]acetate 1,1-dioxide
IR (CHCl₃): 1740, 1690, 1600 cm⁻¹.

(9) Ethyl 2-[3-(4-bromo-2-fluorobenzyl)-1,2,3,4-tetrahydro-8-methoxy-2,4-dioxoquinazolin-1-yl]acetate
IR (Nujol): 1755, 1745, 1700, 1660, 1600 cm⁻¹.

(10) Ethyl 2-[3-(4-chlorobenzyl)-1,2,3,4-tetrahydro-2,4-dioxoquinazolin-1-yl]acetate
mp: 137° C.
IR (Nujol): 1730, 1700, 1670, 1605, 1480 cm⁻¹.

(11) Ethyl 2-[3-(2,6-dichlorobenzyl)-1,2,3,4-tetrahydro-2,4-dioxoquinazolin-1-yl]acetate
mp: 182°-183° C.
IR (Nujol): 1745, 1720, 1680, 1610, 1480 cm⁻¹.

(12) Ethyl 2-[3-(3,5-dichlorobenzyl)-1,2,3,4-tetrahydro-2,4-dioxoquinazolin-1-yl]acetate
mp: 122°-123° C.
IR (Nujol): 1730, 1700, 1660, 1600, 1570, 1480 cm⁻¹.

(13) Ethyl 2-[3-(2,4-dichlorobenzyl)-1,2,3,4-tetrahydro-2,4-dioxoquinazolin-1-yl]acetate
IR (Nujol): 1730, 1710, 1660, 1610 cm⁻¹.

(14) Ethyl 2-[3-(2,5-dichlorobenzyl)-1,2,3,4-tetrahydro-2,4-dioxoquinazolin-1-yl]acetate
IR (Nujol): 1740, 1705, 1660, 1605 cm⁻¹.

(15) Ethyl 2-[1,2,3,4-tetrahydro-3-(4-methoxybenzyl)-2,4-dioxoquinazolin-1-yl]acetate
mp: 135° C.
IR (Nujol): 1730, 1700, 1660, 1600, 1480 cm⁻¹.

(16) Ethyl 2-[1,2,3,4-tetrahydro-3-(1-naphthylmethyl)-2,4-dioxoquinazolin-1-yl]acetate
mp: 164°-167° C.
IR (Nujol): 1745, 1700, 1660, 1605 cm⁻¹.

(17) Ethyl 2-[1,2,3,4-tetrahydro-2,4-dioxo-3-(2-pyridylmethyl)quinazolin-1-yl]acetate
mp: 141°-143° C.
IR (Nujol): 1740, 1700, 1650, 1610 cm⁻¹.

(18) Ethyl 2-[3-(4-bromo-2-fluorobenzyl)-1,2,3,4-tetrahydro-7-methoxy-2,4-dioxoquinazolin-1-yl]acetate
IR (Nujol): 1740, 1690, 1650, 1610 cm⁻¹.

(19) Ethyl 2-[3-(4-bromo-2-fluorobenzyl)-1,2,3,4-tetrahydro-6-methoxy-2,4-dioxoquinazolin-1-yl]acetate
mp: 160°-160.5° C.
IR (Nujol): 1725, 1700, 1655, 1500, 1480 cm⁻¹.

(20) Ethyl 2-[3-(4-bromo-2-fluorobenzyl)-6-chloro-1,2,3,4-tetrahydro-2,4-dioxoquinazolin-1-yl]acetate
mp: 146°-147° C.
IR (Nujol): 1730, 1710, 1675, 1610 cm⁻¹.

(21) Ethyl 2-[3-(2-fluoro-4-iodobenzyl)-1,2,3,4-tetrahydro-2,4-dioxoquinazolin-1-yl]acetate
mp: 157° C.
IR (Nujol): 1750, 1705, 1670, 1610, 1480 cm⁻¹.

(22) Ethyl 2-[3-(4-chloro-2-fluorobenzyl)-1,2,3,4-tetrahydro-2,4-dioxoquinazolin-1-yl]acetate
mp: 144°-145° C.
IR (Nujol): 1730, 1705, 1660, 1610, 1480 cm⁻¹.

(23) Ethyl 2-[3-(4-bromo-3-chlorobenzyl)-1,2,3,4-tetrahydro-2,4-dioxoquinazolin-1-yl]acetate
mp: 128°-129° C.
IR (Nujol): 1735, 1700, 1660, 1600, 1480 cm⁻¹.

(24) Ethyl 2-[3-(2,3-dichlorobenzyl)-1,2,3,4-tetrahydro-2,4-dioxoquinazolin-1-yl]acetate
mp: 158°-160° C.
IR (Nujol): 1740, 1705, 1660, 1605, 1480 cm⁻¹.

(25) Ethyl 2-[1,2,3,4-tetrahydro-3-(4-methylbenzyl)-2,4-dioxoquinazolin-1-yl]acetate
mp: 140°-141° C.
IR (Nujol): 1735, 1700, 1660, 1605, 1480 cm⁻¹.

(26) Ethyl 2-[3-(4-chloro-3-methoxybenzyl)-1,2,3,4-tetrahydro-2,4-dioxoquinazolin-1-yl]acetate
IR (Nujol): 1740, 1705, 1660, 1610 cm⁻¹.

(27) Ethyl 2-[3-(3-chloro-4-methoxybenzyl)-1,2,3,4-tetrahydro-2,4-dioxoquinazolin-1-yl]acetate
IR (Nujol): 1730, 1700, 1660, 1605 cm⁻¹.

(28) Ethyl 2-[1,2,3,4-tetrahydro-2,4-dioxo-3-(2-thienylmethyl)quinazolin-1-yl]acetate
mp: 115°-120° C.
IR (Nujol): 1730, 1700, 1660, 1605 cm⁻¹.

(29) Ethyl 2-[1,2,3,4-tetrahydro-2,4-dioxo-3-(2-naphthylmethyl)quinazolin-1-yl]acetate
mp: 149°-150° C.

(30) Ethyl 2-[3-(4-bromo-2-fluorobenzyl)-5-chloro-1,2,3,4-tetrahydro-2,4-dioxoquinazolin-1-yl]acetate
mp: 186°-187° C.
IR (Nujol): 1740, 1710, 1670, 1590 cm⁻¹.

(31) Ethyl 2-[3-(4-bromo-2-fluorobenzyl)-1,2,3,4-tetrahydro-5-methoxy-2,4-dioxoquinazolin-1-yl]acetate
mp: 166°-168° C.
IR (Nujol): 1735, 1710, 1665, 1600, 1580 cm⁻¹.

(32) Ethyl 2-[3-(4-bromo-2-fluorobenzyl)-7-chloro-1,2,3,4-tetrahydro-2,4-dioxoquinazolin-1-yl]acetate
IR (Nujol): 1740, 1720, 1680, 1610, 1580 cm⁻¹.

(33) Ethyl 2-[7-fluoro-3-(2-fluoro-4-iodobenzyl)-1,2,3,4-tetrahydro-2,4-dioxoquinazolin-1-yl]acetate
IR (Nujol): 1730, 1710, 1680, 1625, 1600, 1570 cm$^{-1}$.

(34) Ethyl 2-[7-bromo-3-(4-bromo-2-fluorobenzyl)-1,2,3,4-tetrahydro-2,4-dioxoquinazolin-1-yl]acetate
mp: 163°-164° C.
IR (Nujol): 1740, 1710, 1675, 1600, 1580, 1490 cm$^{-1}$.

(35) Ethyl 2-[3-(4-bromo-2-fluorobenzyl)-8-chloro-1,2,3,4-tetrahydro-2,4-dioxoquinazolin-1-yl]acetate
mp: 83°-85° C.
IR (Nujol): 1735, 1710, 1660, 1595 cm$^{-1}$.

(36) Ethyl 2-[7-chloro-3-{4-chloro-3-(trifluoromethyl)benzyl}-1,2,3,4-tetrahydro-2,4-dioxoquinazolin-1-yl]acetate
mp: 133°-134° C.
IR (Nujol): 1730, 1700, 1650, 1600 cm$^{-1}$.

(37) Ethyl 2-[3-(4-bromo-2-fluorobenzyl)-1,2,3,4-tetrahydro-7-iodo-2,4-dioxoquinazolin-1-yl]acetate
mp: 169°-169.5° C.
IR (Nujol): 1740, 1710, 1675, 1595, 1575, 1490 cm$^{-1}$.

(38) Ethyl 2-[3-(4-bromo-2-fluorobenzyl)-7-fluoro-1,2,3,4-tetrahydro-2,4-dioxoquinazolin-1-yl]acetate
mp: 144°-145° C.
IR (Nujol): 1700, 1660, 1600, 1370 cm$^{-1}$.

(39) Ethyl 2-[3-(4-bromo-2-fluorobenzyl)-7-trifluoromethyl-1,2,3,4-tetrahydro-2,4-dioxoquinazolin-1-yl]acetate
mp: 150°-152° C.
IR (Nujol): 1700, 1660, 1600, 1370, 1260 cm$^{-1}$.

(40) Ethyl 2-[7-bromo-3-(2-fluoro-4-iodobenzyl)-1,2,3,4-tetrahydro-2,4-dioxoquinazolin-1-yl]acetate
mp: 183°-184° C.
IR (Nujol): 1735, 1710, 1670 cm$^{-1}$.

(41) Ethyl 2-[3-(2-fluoro-4-iodobenzyl)-7-iodo-1,2,3,4-tetrahydro-2,4-dioxoquinazolin-1-yl]acetate
mp: 184°-185° C.
IR (Nujol): 1740, 1715, 1670, 1600, 720 cm$^{-1}$.

(42) Ethyl 2-[3-(4-bromo-2-fluorobenzyl)-6,7-dichloro-1,2,3,4-tetrahydro-2,4-dioxoquinazolin-1-yl]acetate
IR (Nujol): 1730, 1710, 1675, 1575, 1490 cm$^{-1}$.

(43) Ethyl 2-[3-(4-bromo-2-fluorobenzyl)-5,7-dichloro-1,2,3,4-tetrahydro-2,4-dioxoquinazolin-1-yl]acetate
IR (Nujol): 1730, 1720, 1680, 1595, 1570 cm$^{-1}$.

(44) Ethyl 2-[7-chloro-3-(2-fluoro-4-iodobenzyl)-1,2,3,4-tetrahydro-2,4-dioxoquinazolin-1-yl]acetate
IR (Nujol): 1740, 1715, 1675, 1610 cm$^{-1}$.

(45) Ethyl 2-[7-chloro-3-(2-fluoro-3-iodobenzyl)-1,2,3,4-tetrahydro-2,4-dioxoquinazolin-1-yl]acetate
IR (Nujol): 1750, 1720, 1660, 1610 cm$^{-1}$.

(46) Ethyl 2-[7-chloro-3-(3-chloro-4-iodobenzyl)-1,2,3,4-tetrahydro-2,4-dioxoquinazolin-1-yl]acetate
IR (Nujol): 1735, 1710, 1670, 1605, 1580 cm$^{-1}$.

(47) Ethyl 2-[7-chloro-3-{3,5-bis(trifluoromethyl)benzyl}-1,2,3,4-tetrahydro-2,4-dioxoquinazolin-1-yl]acetate
IR (Nujol): 1735, 1710, 1665, 1610, 1580 cm$^{-1}$.

(48) Ethyl 2-[6,7-dichloro-3-(2-fluoro-4-iodobenzyl)-1,2,3,4-tetrahydro-2,4-dioxoquinazolin-1-yl]acetate
mp: 225°-226° C.
IR (Nujol): 1725, 1710, 1675, 1605, 1575 cm$^{-1}$.

EXAMPLE 13

A mixture of ethyl 2-[3-(3,4-dichlorobenzyl)-1,2,3,4-tetrahydro-2,4-dithioxoquinazolin-1-yl]acetate (85 mg), 1N aqueous sodium hydroxide (0.5 ml) and tetrahydrofuran (1 ml) was stirred at room temperature for 20 hours. The reaction mixture was poured into a mixture of ethyl acetate and 0.5N hydrochloric acid. The organic layer was separated, washed with water and brine, and dried over magnesium sulfate. The solvent was removed and the residue was crystallized from chloroform to give 2-[3-(3,4-dichlorobenzyl)-1,2,3,4-tetrahydro-2,4-dithioxoquinazolin-1-yl]acetic acid (36 mg).
mp: 222°-223° C. (dec.).
IR (Nujol): 1710, 1685 cm$^{-1}$.
NMR (DMSO-d$_6$, δ): 5.54 (2H, br s), 5.75 (2H, s), 7.17-7.60 (5H, m), 7.88 (1H, t, J=7 Hz), 8.16 (1H, d, J=8 Hz).

What we claim is:

1. A compound of the formula:

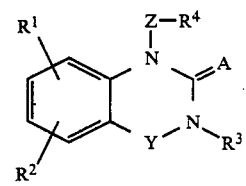

in which
R$^1$ and R$^2$ are each hydrogen, halogen, lower alkoxy or halo(lower)alkyl,
R$^3$ is phenyl(lower)alkyl which may have one or more substituent(s) selected from the group consisting of halogen, lower alkoxy, halo(lower)alkyl and lower alkyl,
R$^4$ is carboxy or protected carboxy,
A is sulfur atom,
Y is carbonyl, thiocarbonyl or sulfonyl and
Z is lower alkylene, and pharmaceutically acceptable salts thereof.

2. A compound of claim 1, wherein
R$^4$ is carboxy or esterified carboxy.

3. A compound of claim 2, wherein
R$^1$ and R$^2$ are each hydrogen, halogen, lower alkoxy or mono(or di or tri)halo(lower)alkyl,
R$^3$ is, phenyl(lower)alkyl, or phenyl(lower)alkyl substituted by one or two substituent(s) selected from the groups consisting of halogen, lower alkoxy, halo(lower)alkyl and lower alkyl.

4. A compound of claim 3, wherein
R$^1$ and R$^2$ are each hydrogen, halogen, lower alkoxy or trihalo(lower)alkyl,
R$^3$ is phenyl(lower)alkyl or phenyl(lower)alkyl substituted by one or two substituent(s) selected from the group consisting of halogen, C$_1$-C$_4$alkoxy, mono(or di or tri) halo (C$_1$-C$_4$)alkyl and C$_1$-C$_4$alkyl, and
R$^4$ is carboxy or lower alkoxycarbonyl.

5. A compound of claim 4, wherein
R$^1$ and R$^2$ are each hydrogen, halogen, C$_1$-C$_4$alkoxy or trihalo(C$_1$-C$_4$)alkyl,
R$^3$ is phenyl(C$_1$-C$_4$)alkyl, or phenyl(C$_1$-C$_4$)alkyl substituted by one or two substituent(s) selected from the groups consisting of halogen, C$_1$-C$_4$alkoxy, trihalo(C$_1$-C$_4$)alkyl and C$_1$-C$_4$alkyl,
R$^4$ is carboxy or C$_1$-C$_4$ alkoxycarbonyl.

6. A pharmaceutical composition for treatment of diabetic complications which comprises an effective amount of a compound of claim 1 in admixture with a pharmaceutically acceptable carrier.

7. A method for the treatment of diabetic complications which comprises administering an effective amount of a compounds of claim 1 to a human or animal.

* * * * *